(12) United States Patent
Myers et al.

(10) Patent No.: US 7,659,383 B2
(45) Date of Patent: Feb. 9, 2010

(54) FELINE 5T4 ANTIGEN

(75) Inventors: Kevin Alan Myers, Oxford (GB); Noel Drury, Oxford (GB); Miles William Carroll, Oxon (GB)

(73) Assignee: Oxford Biomedica (UK) Limited, Oxford (GB)

( * ) Notice: Subject to any disclaimer, the term of this patent is extended or adjusted under 35 U.S.C. 154(b) by 9 days.

(21) Appl. No.: 12/169,222

(22) Filed: Jul. 8, 2008

(65) Prior Publication Data

US 2008/0274542 A1 Nov. 6, 2008

Related U.S. Application Data

(62) Division of application No. 10/416,612, filed as application No. PCT/GB01/05004 on Nov. 13, 2001, now Pat. No. 7,402,666.

(30) Foreign Application Priority Data

Nov. 13, 2000 (WO) .................... PCT/GB00/04317

(51) Int. Cl.
*C07H 21/02* (2006.01)
*C07K 5/00* (2006.01)

(52) U.S. Cl. .................. 536/23.1; 536/23.5; 435/320.1; 435/975

(58) Field of Classification Search ...................... None
See application file for complete search history.

*Primary Examiner*—Sheela J Huff
(74) *Attorney, Agent, or Firm*—Marshall, Gerstein & Borun LLP

(57) ABSTRACT

Canine and feline 5T4 polypeptide sequences and nucleotide sequences encoding them are provided. A vector system comprising a nucleic acid encoding 5T4 and a 5T4-specific agent are also provided.

6 Claims, 12 Drawing Sheets

A
B
C
Figure 1

Figure 3

```
Ca    MPGGCSRGPAAGDGRLRLARLALVLLGWVSSSSLTSWAPSAAASTSPPASAAASAPPPLPG
Fe    MPGGCSRGPAAGDGRLRLARLALVLLGWVSSSSLTSSAP-STSSTSFLASAVSAQPPLPG
Hu    MPGGCSRGPAAGDGRLRLARLALVLLGWVSSSSPTSSASSFSSSAPFLASAVSAQPPLPD
Mu    MPGAGSRGPSAGDGRLRLARLALVLLGWVSASAPSSSVPSSSTSPADFLASGSAQPPPAE

Ca    QCPQPCECSEAARTVKCVNRNLTEVPADLPPYVRNLFLTGNQLAVLPPGAFARRPPLAEL
Fe    QCPQLCECSEAARTVKCVNRNLTEVPADLPPYVRNLFLTGNQLAVLPAGAFARRPPLAEL
Hu    QCPALCECSEAARTVKCVNRNLTEVPTDLPAYVRNLFLTGNQLAVLPAGAFARRPPLAEL
Mu    RCPAACECSEAARTVKCVNRNLLEVPADLPPYVRNLFLTGNQMTVLPAGAFARQPPLADL

Ca    AALNLSGSSLREVCAGAFEHLPSLRQLDLSHNPLGNLSAFAFAGSDASRSGPSPLVELML
Fe    AALNLSGSRLQEVRAGAFEQLPSLRQLDLSHNPLAHLSPFTFSGSNASFSAPSPLVELML
Hu    AALNLSGSRLDEVRAGAFEHLPSLRQLDLSHNPLADLSPFAFSGSNASVSAPSPLVELIL
Mu    EALNLSGNHLKEVCAGAFEHLPGLRRLDLSHNPLTNLSAFVFAGSNASVSAPSPLEELIL

Ca    NHIVPPDDRRQNRS------FEGMVAAALRAGRALRGLQCLELAGNRFLYLPRDVLAQLP
Fe    NHIVPPEDHRHNRS------FEGMVAASLRAGHALRGLQRLELASNHFLFLPRDVLAHLP
Hu    NHIVPPEDERQNRS------FEGMVVAALLAGRALQGLRRLELASNHFLYLPRDVLAQLP
Mu    NHIVPPEDQRQNGSFEGMVAFEGMVAAALRSGLALRGLTRLELASNHFLFLPRDLLAQLP

Ca    GLRHLDLRNNSLVSLTYVSFRNLTHLESLHLEDNALKVLHNATLAELQSLPHVRVFLDNN
Fe    GLRHLDLRNNSLVSLTYVSFRNLTHLQSLHLEDNALKVLHNGTMAELQSLPHVRVFLDNN
Hu    SLRHLDLSNNSLVSLTYVSFRNLTHLESLHLEDNALKVLHNGTLAELQGLPHIRVFLDNN
Mu    SLRYLDLRNNSLVSLTYASFRNLTHLESLHLEDNALKVLHNSTLAEWQGLAHVKVFLDNN

Ca    PWVCDCHMADMVAWLKETEVVPGKAGLTCAFPEKMRNRALLELNSSHLDCDPILPPSLQT
Fe    PWVCDCHMVDMVAWLKETEVVQGKARLACAFPEKMRNRALLELNSSHLECDPILPPSLQT
Hu    PWVCDCHMADMVTWLKETEVVQGKDRLTCAYPEKMRNRVLLELNSADLDCDPILPPSLQT
Mu    PWVCDCYMADMVAWLKETEVVPDKARLTCAFPEKMRNRGLLDLNSSDLDCDAVLPQSLQT

Ca    SYVFLGIVLALIGAIFLLVLYLNRKGIKKWMHNIRDACRDHMEGYHYRYEINADPRLTNL
Fe    SYVFLGIVLALIGAIFLLVLYLNRKGIKKWMHNIRDACRDHMEGYHYRYEINADPRLTNL
Hu    SYVFLGIVLALIGAIFLLVLYLNRKGIKKWMHNIRDACRDHMEGYHYRYEINADPRLTNL
Mu    SYVFLGIVLALIGAIFLLVLYLNRKGIKKWMHNIRDACRDHMEGYHYRYEINADPRLTNL

Ca    SSNSDV
Fe    SSNSDV
Hu    SSNSDV
Mu    SSNSDV
```

Figure 4
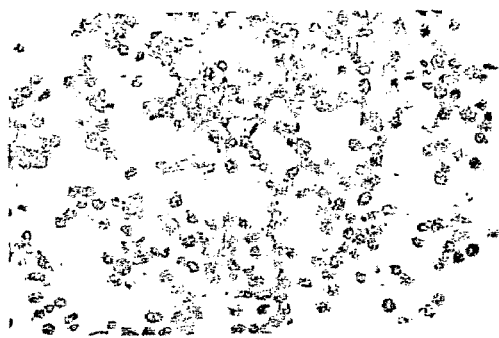
A
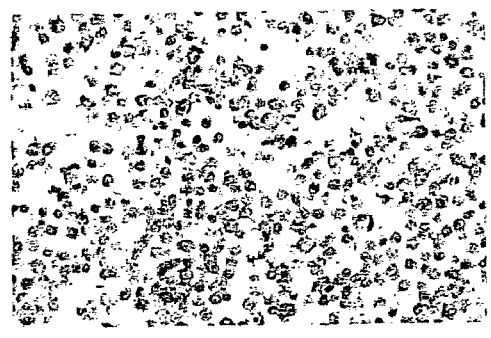
B

Figure 9
pOBMVAt-1
pNEB    Flank 1    MCS    H5    Flank 2    pNEB
pOBMVAt-2
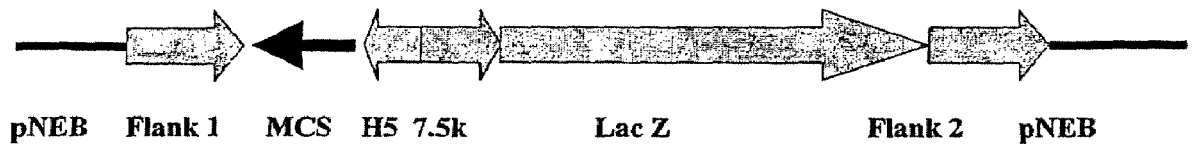
pNEB    Flank 1    MCS    H5  7.5k    Lac Z    Flank 2    pNEB Figure 10
Y1 1:75
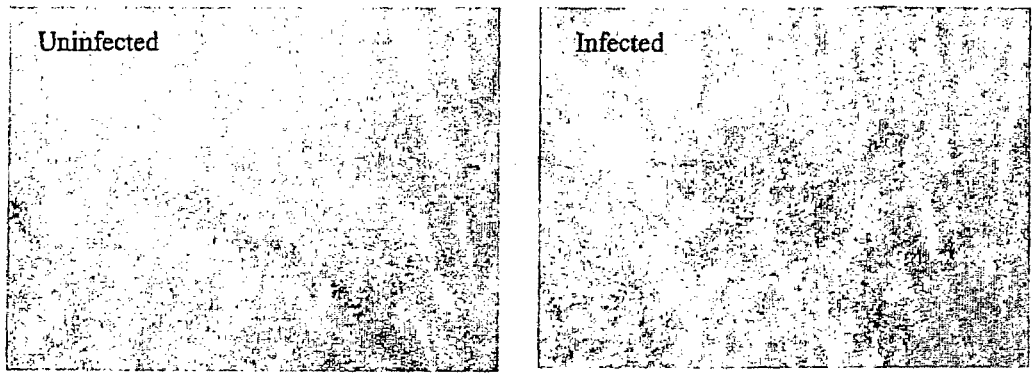
Y3-P3
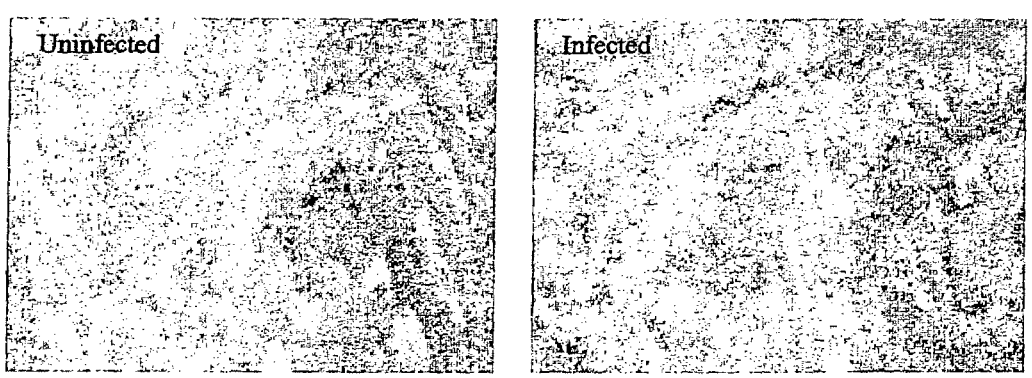

Figure 13
A
B

FELINE 5T4 ANTIGEN

This application is a divisional application of U.S. patent application Ser. No. 10/416,612, filed Oct. 31, 2003, now U.S. Pat. No. 7,402,666, which was the U.S. National Phase under 35 U.S.C. §371 of International Application No. PCT/GB01/05004, filed Nov. 13, 2001, and which claimed the benefit of priority of International Application No. PCT/GB00/04317, filed Nov. 13, 2000.

FIELD OF THE INVENTION

The present invention relates to 5T4 antigens, 5T4-specific agents and their use in immunotherapy.

BACKGROUND TO THE INVENTION

Tumors are relatively common in companion animals (see Mailto and Lagadic (1990) Recueil de Medacine. Veterinaire Special Cancerologie p937-947 for a descriptive epidemiology of canine and feline tumors).

Current methods for treating tumors in cats and dogs include surgery, chemotherapy and radiotherapy. These methods are associated with a number of disadvantages. For example, they all involve a high level of trauma for the patient and they are not always effective in eliminating all the cancerous cells.

An alternative therapeutic approach is immunotherapy which involves the specific or non-specific stimulation of immune reactions of the patient in order to promote the immunological rejection of cancerous cells. There are several methods of immunotherapy:

Non-specific immunotherapy—non-specific stimulation of the immune system (e.g. by using an agent which acts like an adjuvant).

Specific Passive immunotherapy (serotherapy) transferring anti-tumor antibodies to the patient.

Adoptive, immunotherapy—transferring immunocompetent allogenic cells from a healthy individual (eg bone marrow cells)

Specific active immunotherapy—stimulating the immune defenses of the cancer patient by providing the antigens associated with the tumor (e.g. using irradiated cancer cells)

Immunotherapy may be a method of complementary treatment used in combination with surgery, chemotherapy and/or radiotherapy. A study of immunotherapeutic chemical trials in cats and dogs is given in Hayes (1990) Recueil de Medicine Veterinaire 166(11).

An immunotherapeutic approach may be directed against an antigen which is peculiar to the tumor. One strategy for canine and feline cancer immunotherapy would be to identify a tumor-associated antigens (TAAs), expressed on cat or dog tumors, useful for eliciting an anti-tumor immunotherapeutic response.

SUMMARY OF THE INVENTION

The present inventors have shown that a significant proportion of canine and feline tumors express an oncofetal leucine-rich glycoprotein, known as "5T4". There is also presented for the first time the full protein and nucleotide sequences for canine 5T4 and feline 5T4.

The first aspect of the invention relates to canine and feline 5T4 sequences.

In this aspect, the present invention provides i) a canine 5T4 polypeptide having the amino acid sequence shown in SEQ ID No 1 or a variant, homologue, fragment or derivative thereof, and ii) a nucleotide sequence capable of encoding such a canine 5T4 polypeptide. Preferably the nucleotide sequence has the sequence shown as SEQ ID NO 2 or a variant, homologue, fragment or derivative thereof.

The present invention also provides i) a feline 5T4 polypeptide having the amino acid sequence shown in SEQ ID No 3 or a variant, homologue, fragment or derivative thereof; and ii) a nucleotide sequence capable of encoding such a feline 5T4 polypeptide. Preferably the nucleotide sequence has the sequence shown as SEQ ID NO 4 or a variant, homologue, fragment or derivative thereof.

The present invention also provides an agent specific to a canine or feline 5T4 nucleotide sequence. For example, the agent may comprise an antisense sequence capable of binding specifically to the 5T4 sequence.

In a second aspect, the present invention provides a vector system expressing a polynucleotide encoding a canine or feline 5T4 antigen.

Expression of 5T4 antigen in a subject elicits an immunotherapeutic anti-tumor response. Preferably, the viral vector favours CTL responses to expressed antigens, and is advantageously a poxvirus vector, such as a vaccinia virus vector. Further vectors, both viral and non-viral, which are suitable for delivering 5T4 antigen are described below.

In a third aspect, the invention provides an agent capable of binding specifically to canine or feline 5T4 protein. The agent may be an antibody. For example, the agent may be an antibody raised against the canine or feline 5T4 protein (or fragment thereof) of the first aspect of the invention.

Thus, the invention provides a kit comprising a vector according to the second aspect of the invention and an agent according to the third aspect of the invention, for simultaneous, separate, or sequential use, preferably for use in the treatment of tumors.

Thus, the invention provides a kit comprising a vector according to the second aspect of the invention and an agent according to the third aspect of the invention, for simultaneous, separate, or sequential use, preferably for use in the treatment of tumors.

In a fourth aspect the present invention provides a vaccine, priming composition or boosting composition comprising such a polypeptide, polynucleotide, vector system or agent. The vaccine, priming or boosting composition may comprise one or more adjuvants.

It has been found that multiple-dose procedures are often more effective at generating an immune response that a single administration of vaccine. Prime-boost regimes may be homologous (where the same composition is administered two or more times) or heterologous.

An example of a heterologous prime-boost regime would be the administration of at least one dose of a DNA vaccine, followed by at least one dose of a viral vaccine. An example of a homologous prime-boost regime is repeated doses of a viral vector system.

In this respect, the present invention also comprises a kit which comprises:

a first composition comprising a polynucleotide encoding a 5T4 antigen, and a second composition comprising a vector system according to the second aspect of the invention for simultaneous, separate or sequential administration to a subject.

The first composition may, for example, be a naked DNA vector.

In a fifth aspect, the present invention provides the use of such a 5T4 antigen, polypeptide, polynucleotide, vaccine, priming composition, boosting composition or kit in the manufacture of a medicament for the prevention and/or treatment of a disease in a subject.

The present invention also provides a method for the treatment and/or prevention of a disease in a subject which comprises the step of administration of such a 5T4 antigen, protein, polynucleotide, vaccine, priming composition, boosting composition to the subject.

Preferably the method of the fifth aspect of the invention is a method for immunotherapy of a tumor in a subject.

DETAILED DESCRIPTION OF THE INVENTION

Other aspects of the present invention are presented in the accompanying claims and in the following description and drawings. These aspects are presented under separate section headings. However, it is to be understood that the teachings under each section are not necessarily limited to that particular section heading.

5T4 Proteins

The first aspect of the invention relates to canine and feline 5T4 proteins and their associated polynucleotides.

In humans, the oncofetal leucine-rich glycoprotein, 5T4, is expressed by a wide variety of carcinomas, but on normal adult tissues expression is restricted to the placenta (with low levels also being found on a few specialised epithelia. Presence of the antigen on cancer cells is associated with metastasis and has been shown to be an independent indicator of poor prognosis in a number of different cancers.

The human tumor-associated antigen 5T4 is a 72 kDa glycoprotein and has been characterized (for example, in WO89/07947). The full nucleic acid sequence of human 5T4 is known (iGeniBank accession no. Z29083; Myers et al., 1994 J Biol Chem 169: 9319-24).

WO 00/29428 describes the partial sequence of canine 5T4.

The present invention provides, for the first time, the full amino acid and nucleic acid sequences for canine and human 5T4. Despite the fact the human and partial canine sequences were available, isolation and cloning of the full canine and feline sequences was not straightforward. In this respect a number of attempts were made to isolate the canine gene by PCR using primers based on the human sequence immediately outside the coding region. Such attempts failed due to unexpected differences between the human and canine sequences immediately upstream of the start codon.

```
                                                  (SEQ ID NO:5)
CCCAGCTCCGGGGAGCGCCGCGCCGCGCCGCGATG  Canine (SEQ ID NO:6)
       AGCTCCGGGGAAACGCGAGCC            failed PRIMER (SEQ ID NO:7)
CCCAGCTCCGGGGAAACGCGAGCCGCGATG          Human
```

Amino Acid Sequences

As used herein, the term "amino acid sequence" refers to peptide, polypeptide sequences, protein sequences or portions thereof.

The present invention covers variants, homologues or derivatives of the amino acid sequences presented herein, as well as variants, homologues or derivatives of the nucleotide sequence coding for those amino acid sequences.

In the context of the present invention, a homologous sequence is taken to include an amino acid sequence which is at least 75, 85 or 90% identical, preferably at least 95 or 98% identical at the amino acid level over at least, for example, the amino acid sequence as set out in SEQ ID No 1 or SEQ ID No 3 of the sequence listing herein. In particular, homology should typically be considered with respect to those regions of the sequence known to be essential for binding specificity (such as amino acids at positions) rather than nonessential neighbouring sequences. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 760). However it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8 and tatiana@ncbi.nim.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

The terms "variant" or "derivative" in relation to the amino acid sequences of the present invention includes any substitution of, variation of, modification of, replacement of, deletion of or addition of one (or more) amino acids from or to the sequence providing the resultant amino acid sequence has a binding specificity, preferably having at least the same binding specificity as the amino acid sequence set out in SEQ ID No 1 or SEQ ID No 3 of the sequence listing herein.

SEQ ID No 1 or SEQ ID No 3 of the sequence listing herein may be modified for use in the present invention. Typically, modifications are made that maintain the binding specificity of the sequence. Amino acid substitutions may be made, for example from 1, 2 or 3 to 10 or 20 substitutions provided that the modified sequence retains the required binding specificity. Amino acid substitutions may include the use of non-naturally occurring analogues.

The 5T4 polypeptide of the present invention may also have deletions, insertions or substitutions of amino acid residues which produce a silent change and result in a functionally equivalent molecule. Deliberate amino acid substitutions may be made on the basis of similarity in polarity, charge, solubility, hydrophobicity, hydrophilicity, and/or the amphipathic nature of the residues as long as the binding specificity of the 5T4 polypeptide is retained. For example, negatively charged amino acids include aspartic acid and glutamic acid; positively charged amino acids include lysine and arginine; and amino acids with uncharged polar head groups having similar hydrophilicity values include leucine, isoleucin, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Preferably, the 5T4 sequence is prepared by use of recombinant techniques.

With regard to a fragment of the canine 5T4 sequence, preferably the fragment comprises at least one, preferably some, most preferably all of the amino adds 1-182 and/or 297-420 shown in SEQ ID No 1.

Nucleotide Sequences

It will be understood by a skilled person that numerous different nucleotide sequences can encode the same 5T4 polypeptide of the present invention as a result of the degeneracy of the genetic code. In addition, it is to be understood that skilled persons may, using routine techniques, make nucleotide substitutions that do not affect the 5T4 polypeptide encoded by the nucleotide sequence of the present invention to reflect the codon usage of any particular host organism in which the 5T4 polypeptide of the present invention is to be expressed.

The terms "variant", "homologue" or "derivative" in relation to the nucleotide sequence set out in SEQ ID No 15 (see FIG. 26) of the present invention includes any substitution of, variation of, modification of replacement of, deletion of or addition of one (or more) nucleic acid from or to the sequence providing the resultant nucleotide sequence codes for a canin or felin 5T4 polypeptide, preferably a polypeptide as set out in SEQ ID No 1 or 3 of the sequence listing of the present invention.

As indicated above, with respect to sequence homology, preferably there is at least 75%, more preferably at least 85%, more preferably at least 90% homology to the sequences shown in the sequence listing herein. More preferably there is at least 95%, more preferably at least 98%, homology. Nucleotide homology comparisons may be conducted as describe above. A preferred sequence comparison program is the GCG Wisconsin Bestfit program described above. The default scoring matrix has a match value of 10 for each identical nucleotide and −9 for each mismatch. The default gap creation penalty is −50 and the default gap extension penalty is −3 for each nucleotide.

The present invention also encompasses nucleotide sequences that are capable of hybridising selectively to the sequences presented herein, or any variant, fragment or derivative thereof, or to the complement of any of the above. Nucleotide sequences are preferably at least 15 nucleotides in length, more preferably at least 20, 30, 40 or 50 nucleotides in length.

With regard to a fragment of the canine 5T4 sequence, preferably the fragment comprises at least one, preferably some, most preferably all of the nucleic acids 1-546 and/or 890-1263 shown in SEQ ID No 15.

Hybridisation

The term 'hybridization' as used herein shall include "the process by which a strand of nucleic acid joins with a complementary strand through base pairing".

Nucleotide sequences of the invention capable of selectively hybridising to the nucleotide sequences presented herein, or to their complement, will be generally at least 75%, preferably at least 85 or 90% and more preferably at least 95% or 98% homologous to the corresponding nucleotide sequences presented herein over a region of at least 20, preferably at least 25 or 30, for instance at least 40, 60 or 100 or more contiguous nucleotides. Preferred nucleotide sequences of the invention will comprise-regions homologous to the nucleotide sequence set out in SEQ ID No 2 or SEQ ID No 4 of the sequence listings of the present invention preferably at least 80 or 90% and more preferably at least 95% homologous to the nucleotide sequence set out in SEQ ID NO 2 or 4 of the sequence listings of the present invention.

The term "selectively hybridizable" means that the nucleotide sequence used as a probe is used under conditions where a target nucleotide sequence of the invention is found to hybridize to the probe at a level significantly above background. The background hybridization may occur because of other nucleotide sequences present, for example, in the cDNA or genomic DNA library being screened. In this event, background implies a level of signal generated by interaction between the probe and a non-specific DNA member of the library which is less than 10 fold, preferably less than 100 fold as intense as the specific interaction observed with the target DNA. The intensity of interaction may be measured, for example, by radiolabelling the probe, e.g. with $^{32}$P.

Hybridization conditions are based on the meting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridization can be used to identify or detect identical nucleotide sequences while an intermediate (or low) stringency hybridization can be used to identify or detect similar or related polynucleotide sequences.

In a preferred aspect, the present invention covers nucleotide sequences that can hybridise to the nucleotide sequence of the present invention under stringent conditions (e.g. 65° C. and 0.1×SSC (1×SSC=0.15 M NaCl, 0.015 M Na$_3$Citrate pH 7.0). Where the nucleotide sequence of the invention is double-stranded, both strands of the duplex, either individually or in combination, are encompassed by the present invention. Where the nucleotide sequence is single-stranded, it is to be understood that the complementary sequence of that nucleotide sequence is also included within the scope of the present invention.

Nucleotide sequences which are not 100% homologous to the sequences of the present invention but fall within the scope of the invention can be obtained in a number of ways. Other variants of the sequences described herein may be obtained for example by probing DNA libraries made from a range of sources. In addition, other viral/bacterial, or cellular homologues particularly cellular homologues found in mammalian cells (e.g. rat, mouse, bovine and primate cells), may be obtained and such homologues and fragments thereof. In general will be capable of selectively hybridising to the sequences shown in the sequence listing herein. Such sequences may be obtained by probing cDNA libraries made from or genomic DNA libraries from other animal species, and probing such libraries with probes comprising all or part of the nucleotide sequence set out in SEQ ID No 2 or SEQ ID No 4 of the sequence listings of the present invention under conditions of medium to high stringency. Similar considerations apply to obtaining species homologues and allelic variants of the amino add and/or nucleotide sequences of the present invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used. The primers used in degenerate PCR will contain one or more degenerate positions and will be used at stringency conditions lower than those used for cloning sequences with single sequence primers against known sequences.

Alternatively, such nucleotide sequences may be obtained by site directed mutagenesis of characterised sequences, such as the nucleotide sequence set out in SEQ ID No 2 or SEQ ID No 4 of the sequence listings of the present invention. This may be useful where for example silent codon changes are required to sequences to optimise codon preferences for a particular host cell in which the nucleotide sequences are being expressed. Other sequence changes may be desired in order to introduce restriction enzyme recognition sites, or to ater the activity of the 5T4 polypeptide encoded by the nucleotide sequences.

The nucleotide sequences of the present invention may be used to produce a primer, e.g. a PCR primer, a primer for an alternative amplification reaction, a probe e.g. labelled with a revealing label by conventional means using radioactive or non-radioactive labels, or the nucleotide sequences may be cloned into vectors. Such primers, probes and other fragments will be at least 15, preferably at least 20, for example at least 25, 30 or 40 nucleotides in length, and are also encompassed by the term nucleotide sequence of the invention as used herein.

The nucleotide sequences such as a DNA polynucleotides and probes according to the invention may be produced recombinantly, synthetically, or by any means available to those of skill in the art. They may also be cloned by standard techniques.

In general, primers will be produced, by synthetic means, involving a step wise manufacture of the desired nucleic acid sequence one nucleotide at a time. Techniques for accomplishing this using automated techniques are readily available in the art.

Longer nucleotide sequences will generally be produced using recombinant means, for example using a PCR (polymerase chain reaction) cloning techniques. This will involve making a pair of primers (e.g. of about 15 to 30 nucleotides) flanking a region of the targeting sequence which it is desired to clone, bringing the primers into contact with mRNA or cDNA obtained from an animal or human cell, performing a polymerase chain reaction (PCR) under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Due to the inherent degeneracy of the genetic code, other DNA sequences which encode substantially the same or a functionally equivalent amino acid sequence, may be used to clone and express the 5T4 polypeptide. As will be understood by those of skill in the art, it may be advantageous to produce the 5T4 polypeptide—encoding nucleotide sequences possessing non-naturally occurring codons. Codons preferred by a particular prokaryotic or eukaryotic host (Murray E et al (1989) Nuc Acids Res 17:477-508); can be selected, for example, to increase the rate of the 5T4 polypeptide expression or to produce recombinant RNA transcripts having desirable properties, such as a longer half-life, than transcripts produced from naturally occurring sequence.

Agent/Antibody

The fourth aspect of the invention provides an agent capable of binding specifically to canine or feline 5T4 protein. The agent may be an antibody.

WO 00/29428 describes antibodies which are capable of binding specifically to human 5T4. The present inventors have demonstrated that these antibodies do not cross-react with feline or canine 5T4.

As used herein, "antibody" includes a whole immunoglobulin molecule or a part thereof or a bioisostere or a mimetic thereof or a derivative thereof or a combination thereof. Examples of a part thereof include: Fab, F(ab)'$_2$, and Fv. Examples of a bioisostere include single chain Fv (ScFv) fragments, chimeric antibodies, bifunctional antibodies.

The term "mimetic" relates to any chemical which may be a peptide, polypeptide, antibody or other organic chemical which has the same binding specificity as the antibody.

The term "derivative" as used herein includes chemical modification of an antibody. Illustrative of such modifications would be replacement of hydrogen by an alkyl, acyl, or amino group.

A whole immunoglobulin molecule is divided into two regions: binding (Fab) domains that interact with the antigen and effector (Fc) domains that signal the initiation of processes such as phagocytosis. Each antibody molecule consists of two classes of polypeptide chains, light (L) chains and heavy (H) chairs. A single antibody has two identical copies of the L chain and two of the H chain. The N-terminal domain from each chain forms the variable regions, which constitute the antigen-binding sites. The C-terminal domain is called the constant region. The variable domains of the H ($V_H$) and L ($V_L$) chains constitute an Fv unit and can interact closely to form a single chain Fv (ScFv) unit. In most H chains, a hinge region is found. This hinge region is flexible and allows the Fab binding regions to move freely relative to the rest of the molecule. The hinge region is also the place on the molecule most susceptible to the action of protease which can split the antibody into the antigen binding site (Fab) and the effector (Fc) region.

The domain structure of the antibody molecule is favourable to protein engineering, facilitating the exchange between molecules of functional domains carrying antigen-binding activities (Fabs and Fvs) or effector functions (Fc). The structure of the antibody also makes it easy to produce antibodies with an antigen recognition capacity joined to molecules such as toxins, lymphocytes or growth factors.

Chimeric antibody technology may involve the transplantation of antibody variable domains from one species (for example, a mouse) onto antibody constant domains from another species (for example a cat or dog).

Fab, Fv, and single chain Fv (ScFv) fragments with VH and VL joined by a polypeptide linker exhibit specificities and affinities for antigen similar to the original monoclonal antibodies. The ScFv fusion proteins can be produced with a non-antibody molecule attached to either the amino or carboxy terminus. In these molecules, the Fv can be used for specific targeting of the attached molecule to a cell expressing the appropriate antigen. Bifunctional antibodies can also be created by engineering two different binding specificities into a single antibody chain. Bifunctional Fab, Fv and ScFv antibodies may comprise engineered domains such as CDR grafted or humanised domains.

A large number of monoclonal antibodies and immunoglobulin-like molecules are known which bind specifically to antigens present on the surfaces of particular cell types. Procedures for identifying, characterising, cloning and engineering these molecules are well established, for example using hybridomas derived from mice or transgenic mice, phage-display libraries or scFv libraries. Genes encoding immunoglobulins or immunoglobulin-like molecules can be expressed in a variety of heterologous expression systems. Large to glycosylated proteins including immunoglobulins are efficiently secreted and assembled from eukaryotic cells, particularly mammalian cells. Small, non-glycosylated fragments such as Fab, Fv, or scFv fragments can be produced in functional form in mammalian cells or bacterial cells.

The antigen-binding domain may be comprised of the heavy and light chains of an immunoglobulin, expressed from separate genes, or may use the light chain of an immunoglobulin and a truncated heavy chain to form a Fab or a F(ab)'$_2$ fragment. Alternatively, truncated forms of both heavy and light chains may be used which assemble to form a Fv fragment. An engineered scFv fragment may also be used, in which case, only a single gene is required to encode the antigen-binding domain.

In a preferred aspect, the present invention provides an ScFv antibody (ScFv Ab), capable of recognising canine 5T4 or feline 5T4.

The invention also provides a nucleotide sequence capable of encoding such an antibody or derivative thereof and a vector comprising such a nucleic acid sequence. The antibody or its precursor (i.e. nucleic acid encoding the antibody) may be used in a method to treat and/or prevent a disease.

For example, an ScFv Ab can be directly administered to a cat or dog either as a peptide (synthetically or genetically expressed) or as "naked DNA" (for example, in a plasmid) or via a delivery vehicle such as a viral vector comprising the nucleotide sequence encoding the ScFv Ab.

The antibody, or derivative thereof (for example anti-5T4 scFvs) may be used as an 5T4 targeting molecule. For example, they may be used to (i) to target natural or exogenous 5T4 in situ and/or (ii) deliver immune enhancer molecules, such as B7.1, to natural or exogenous 5T4 in situ (Carroll et al. (1998) J Natl Cancer Inst 90(24):1881-7). This potentiates the immunogenicity of 5T4 in the subject.

The term "binds specifically" as used herein is intended to mean that the agent preferentially binds to canine and/or feline c5T4 than to human 5T4. Preferably the agent preferentially binds to either canine or feline 5T4 and does not bind or binds significantly less well to the other protein. If the agent is an antibody it may be raised against canine or feline 5T4 or one or more fragments thereof.

Vector Systems

The second aspect of the invention relates to a vector system expressing a polynucleotide encoding a canine or feline 5T4 antigen.

As used herein, a "vector system" may be any agent capable of delivering or maintaining nucleic acid in a host cell, and includes viral vectors, plasmids, naked nucleic acids, nucleic-acids complexed with polypeptide or other molecules and nucleic acids immobilised onto solid phase particles. Such vectors are described in detail below. It will be understood that the present invention, in its broadest form, is not limited to any specific vector for delivery of the 5T4-encoding nucleic acid.

The 5T4 antigen is "expressed" in accordance with the present invention by being produced in the cells of a host organism as a result of translation, and optionally transcription, of the nucleic acid encoding the 5T4 antigen. Thus, 5T4 antigen is produced in situ in the cell. Since 5T4 is a transmembrane protein, the extracellular portion thereof is displayed on the surface of the cell in which it is produced. If necessary, therefore, the term "expression" includes the provision of the necessary signals to ensure correct processing of the 5T4 antigen such that it is displayed on the cell surface and can interact with the host immune system.

Vector

As it is well known in the art, a vector is a tool that allows or facilitates the transfer of an entity from one environment to another. In accordance with the present invention, and by way of example, some vectors used in recombinant DNA techniques allow entities, such as a segment of DNA (such as a heterologous DNA segment, such as a heterologous cDNA segment), to be transferred into a host and/or a target cell for the purpose of replicating the vectors comprising the nucleotide sequences of the present invention and/or expressing the proteins of the invention encoded by the nucleotide sequences of the present invention. Examples of vectors used in recombinant DNA techniques include but are not limited to plasmids, chromosomes, artificial chromosomes or viruses.

"Naked DNA"

The vectors comprising nucleotide sequences encoding 5T4 polypeptide or 5T4-specific agent of the present invention may be administered directly as "a naked nucleic acid construct", preferably further comprising flanking sequences homologous to the host cell genome.

As used herein, the term "naked DNA" refers to a plasmid comprising a nucleotide sequences encoding a 5T4 polypeptide or 5T4-specific agent of the present invention together with a short promoter region to control its production. It is called "naked" DNA because the plasmids are not carried in any delivery vehicle. When such a DNA plasmid enters a host cell, such as a eukaryotic cell, the proteins it encodes are transcribed and translated within the cell.

Non-Viral Delivery

Alternatively, the vectors comprising nucleotide sequences of the present invention may be introduced into suitable host cells using a variety of non-viral techniques known in the art, such as transfection, transformation, electroporation and biolistic transformation.

As used herein, the term "transfection" refers to a process using a non-viral vector to deliver a gene to a target mammalian cell.

Typical transfection methods include electroporation, DNA biolistics, lipid-mediated transfection, compacted DNA-mediated transfection, liposomes, immunoliposomes, lipofectin, cationic agent-mediated, cationic facial amphiphiles (CFAs) (Nature Biotechnology 1996 14; 556), multivalent cations such as spermine; cationic lipids or polylysine, 1,2,-bis (oleoyloxy)-3-(trimethylammonio) propane (DOTAP)-cholesterol complexes (Wolff and Trubetskoy 1998 Nature Biotechnology 16: 421) and combinations thereof.

Uptake of naked nucleic acid constructs by mammalian cells is enhanced by several known transfection techniques for example those including the use of transfection agents. Example of these agents include cationic agents (for example calcium phosphate and DEAE-dextran) and lipofectants (for example Lipofectam™ and Transfectam™). Typically, nucleic acid constructs are mixed with the transfection agent to produce a composition.

Viral Vectors

Alternatively, the vectors comprising nucleotide sequences of the present invention may bee introduced into suitable host cells using a variety of viral techniques which are known in the art, such as for example infection with recombinant viral vectors such as retroviruses, herpes simplex viruses and adenoviruses.

Preferably the vector is a recombinant viral vectors. Suitable recombinant viral vectors include but are not limited to adenovirus vectors, adeno-associated viral (AAV) vectors, herpes-virus vectors, a retroviral vector, lentiviral vectors, baculoviral vectors, pox viral vectors or parvovirus vectors (see Kestler et al 1999 Human Gene Ther 10(10): 1619-32). In the case of viral vectors, gene delivery is mediated by viral infection of a target cell.

The term "vector system" when applied to viral vector includes a vector particle capable of infecting a mammalian cell. There is also provided kits for the production of the vector particle, the constituents of which will depend on the viral vector type on which the system is based. For example, a kit for a retrovirus may comprise:

i) a viral genome comprising a 5T4 nucleotide; and either
ii) one or more producer plasmids and a host cell, or
iii) a producer cell.

Retroviral Vectors

Examples of retroviruses include but are not limited to: murine leukemia virus (MLV), human immunodeficiency virus (HIV), equine infectious anaemia virus (EJAV), mouse mammary tumor virus (MMTV), Rous sarcoma virus (RSV), Fujinami sarcoma virus (FuSV), Moloney murine leukemia virus (Mo-MLV), FBR murine osteosarcoma virus. (FBR MSV), Moloney murine sarcoma virus (Mo-MSV), Abelson murine leukemia virus (A-MLV); Avian myelocytomatosis virus-29 (MC29), and Avian erythroblastosis virus (AEV).

Preferred vectors for use in accordance with the present invention are recombinant viral vectors, in particular recombinant retroviral vectors (RRV) such as lentiviral vectors.

The term "recombinant retroviral vector" (RRV) refers to a vector with sufficient retroviral genetic information to allow packaging of an RNA genome, in the presence of packaging components, into a viral particle capable of infecting a target cell. Infection of the target cell includes reverse transcription and integration into the target cell genome. The RRV carries non-viral coding sequences which are to be delivered by the vector to the target cell. An RRV is incapable of independent replication to produce infectious retroviral particles within the final target cell. Usually the RRV lacks a functional gag-pol and/or env gene and/or other genes essential for replication. The vector of the present invention may be configured as a split-intron vector. A split intron vector is described in PCT patent application WO 99/15683.

A detailed list of retroviruses may be found in Coffin et al ("Retroviruses" 1997 Cold Spring Harbour Laboratory Press Eds: J M Coffin, S M Hughes, H E Varmus pp 758-763).

Lentiviral Vectors

Lentiviruses can be divided into primate and non-primate groups. Examples of primate lentiviruses include but are not limited to: the human immunodeficiency virus (HIV), the causative agent of human auto-immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

A distinction between the lentivirus family and other types of retroviruses is that lentivirus s have the capability to infect both dividing and non-dividing cells (Lewis et al 992 EMBO. J 11: 3053-3058; Lewis and Emerman 1994 J. Virol. 68: 510-516). In contrast, other retroviruses—such as MLV—are unable to infect non-dividing cells such as those that make up, for example, muscle, brain, lung and liver tissue.

Adenoviruses

In one embodiment of the present invention, the features of adenoviruses may be combined with the genetic stability of retroviruses/lentiviruses which can be used to transduce target cells to become transient retroviral producer cells capable of stably infect neighbouring cells.

Such retroviral producer cells which are engineered to express a 5T4 polypeptide or 5T4-specific agent of the present invention can be implanted in organisms such as animals or humans for use in the treatment of disease such as cancer.

POX Viruses

Preferred vectors for use in accordance with the present invention are recombinant pox viral vectors such as fowl pox virus (FPV), entomopox virus, vaccinia virus such as NYVAC, canarypox virus, Modified vaccinia Ankara (MVA) or other non-replicating viral vector systems such as those described for example in WO 95/30018.

In a preferred embodiment the vector is MVA. General teachings on pox vectors and MVA can be found in WO 00/29428.

Expression of 5T4 proteins or antigens in recombinant pox viruses, such as vaccinia viruses, requires the ligation of vaccinia promoters to the nucleic acid encoding 5T4. In order to do this a transfer plasmid is constructed which contains at least one nucleic acid which codes for a 5T4 antigen flanked by MVA DNA sequences. When this transfer plasmid is introduced into cells infected with MVA, homologous recombination occurs causing the 5T4 nucleotide to be inserted into the MVA virus (Mackett et al 1982 PNAS 79: 7415-7419).

The transfer plasmid contains sequences flanking the left and the right side of a naturally occurring deletion, e.g. deletion II, within the MVA genome (Altenburger, W., Suter, C. P. and Altenburger J. (1989) Arch. Virol. 105, 15-27). The foreign DNA sequence is inserted between the sequences flanking the naturally occurring deletion.

For the expression of at least one nucleic acid, it is necessary for regulatory sequences, which are required for the transcription of the nucleic acid to be present upstream of the nucleic acid. Such regulatory sequences are known to those skilled in the art, and includes for example those of the vaccinia 11 kDa gene as are described in EP-A-198,328, and those of the 7.5 kDa gene (EP-A-110,385).

The construct can be introduced into the MVA infected cells by transfection, for example by means of calcium phosphate precipitation (Graham et al Virol. 52, 456-467 [1973; Wigler et al Cell 777-785 [1979] by means of electroporation (Neumann et al EMBO J. 1, 841-845 [1982]), by microinjection (Graessmann et al Meth. Enzymology 101, 482-492 (1983)), by means of liposomes (Straubinger et al Methods in Enzymology 101, 512-527 (1983)), by means of spheroplasts (Schaffner, Proc. Natl. Acad. Sci. USA 77, 2163-2167 (1980)) or by other methods known to those skilled in the art. Transfection by means of liposomes is preferred.

Once the construct has been introduced into the eukaryotic cell and the 5T4 antigen DNA has recombined with the viral DNA, the desired recombinant vaccinia virus, can be isolated, preferably with the aid of a marker (Nakano et al Proc. Natl. Acad. Sci. USA 79, 1593-1596 [1982], Franke et al Mol. Cell. Biol. 1918-1924 [1985], Chakrabarti et al Mol. Cell. Biol. 3403-3409 [1985], Fathi et al Virology 97-105 [1986]).

The present invention thus also provides a kit which comprises a transfer plasmid which comprises a polynucleotide encoding a 5T4 antigen flanked by MVA DNA sequences.

The kit may also include a cell infected with MVA, such as BHK-21 or CEF cells, or wild-type MVA stock for infection purposes.

The nucleic acid must be inserted into a region (insertion region) in the virus which does not affect virus viability of the resultant recombinant virus. Such regions can be readily identified in a virus by, for example, randomly testing segments of virus DNA for regions that allow recombinant formation without seriously affecting virus viability of the recombinant. One region that can readily be used and is present in many viruses is the thymidine kinase (TK) gene. For example, the TK gene has been found in all pox virus genomes examined [leporipoxvirus: Upton, et al J. Virology 60:920 (1986) (shope fibroma virus); capripoxvirus: Gershon, et al J. Gen. Virol. 70:525 (1989) (Kenya sheep-I); orthopoxvirus: Weir et al J. Virol 46:530 (1983) (vaccinia); Esposito, et al Virology 135:561 (1984) (monkeypox and variola virus); Hruby, et al PNAS, 80:3411(1983) (vaccinia); Kilpatrick, et al Virology 143:399 (1985) (Yaba monkey tumor virus); avipoxvirus: Binns, et al J. Gen Virol 69:1275 (1988) (fowlpox); Boyle, et al Virology 156:355 (1987) (fowlpox); Schnitzlein, et al J. Virological Method, 20:341 (1988) (fowlpox, quailpox); entomopox (Lytvyn et al J. Gen. Virol 73:3235-3240 (1992)].

A promoter can be selected depending on the host and the target c II type. For example in poxviruses, pox viral promoters should be used, such as the vaccinia 7.5K, or 40K or fowlpox C1. Artificial constructs containing appropriate pox sequences can also be used. Enhancer elements can also be used in combination to increase the level of expression. Furthermore, the use of inducible promoters, which are also well known in the art, are preferred in some embodiments. A particularly preferred promoter is a modified H5 promoter (Wyatt et al (1996) Vaccine (4) 1451-1458).

Hybrid Viral Vectors

In a further broad aspect, the present invention provides a hybrid viral vector system for in vivo delivery of a nucleotide sequence encoding a 5T4 polypeptide or 5T4-specific agent of the present invention, which system comprises one or more primary viral vectors which encode a secondary viral vector, the primary vector or vectors capable of infecting a first target cell and of expressing therein the secondary viral vector, which secondary vector is capable of transducing a secondary target cell.

Preferably the primary vector is obtainable from or is based on an adenoviral vector and/or the secondary viral vector is obtainable from or is based on a retroviral vector preferably a lentiviral vector.

Targeted Vector

The term "targeted vector" refers to a vector whose ability to infect/transfect/transduce a cell or to be expressed in a host and/or target cell is restricted to certain cell types within the host organism, usually cells having a common or similar phenotype.

Replication Vectors

The nucleotide sequences encoding the 5T4 polypeptide or 5T4-specific agent of the present invention may be incorporated into a recombinant replicable vector. The vector may be used to replicate the nucleotide sequencer in a compatible host cell. Thus in one embodiment of the present invention, the invention provides a method of making the 5T4 polypeptide or 5T4 specific agent of the present invention by introducing a nucleotide sequence of the present invention into a replicable vector, introducing the vector into a compatible host cell, and growing the host-cell under conditions which bring about replication of the vector. The vector may be recovered from the host cell.

Expression Vector

Preferably, a nucleotide sequence of present invention which is inserted into a vector is operably linked to a control sequence that is capable of providing for the expression of the coding sequence, such as the coding sequence of the 5T4 polypeptide or 5T4-specific agent of the present invention by the host cell, i.e. the vector is an expression vector. The 5T4 polypeptide or 5T4-specific agent produced by a host recombinant cell may be secreted or may be contained intracellularly depending on the sequence and/or the vector used. As will be understood by those of skill in the art, expression vectors containing the 5T4 polypeptide or 5T4-specific agent coding sequences can be designed with signal sequences which direct secretion of the 5T4 polypeptide or 5T4-specific agent coding sequences through a particular prokaryotic or eukaryotic cell membrane.

Expression In Vitro

The vectors of the present invention may be transformed or transfected into a suitable host cell and/or a target cell as described below to provide for expression of a 5T4 polypeptide or 5T4-specific agent of the present invention. This process may comprise culturing a host cell and/or target cell transformed with an expression vector under conditions to provide for expression by the vector of a coding sequence encoding the 5T4 polypeptide or 5T4-specific agent and optionally recovering the expressed 574 polypeptide or 5T4-specific agent. The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. The expression of the 5T4 polypeptide or 5T4-specific agent of the invention may be constitutive such that they are continually produced, or inducible, requiring a stimulus to initiate expression. In the case of inducible expression, 5T4 polypeptide or 5T4-specific agent production can be initiated when required by, for example, addition of an inducer substance to the culture medium, for example dexamethasone or IPTG.

Host/Target Cells

Host and/or target cells comprising nucleotide sequences of the present invention may be used to express the 5T4 polypeptide or 5T4-specific agents of the present invention under in vitro, in vivo and ex vivo conditions.

The term "host cell and/or target cell" includes any cell derivable from a suitable organism which a vector is capable of transfecting or transducing. Examples of host and/or target cells can include but are not limited to cells capable of expressing the 5T4 polypeptide or 5T4 specific agent of the present invention under in vitro, in vivo and ex vivo conditions. Examples of such cells include but are not limited to macrophages, endothelial cells or combinations thereof. Further examples include respiratory airway epithelial cells, hepatocytes, muscle cells, cardiac myocytes, synoviocytes, primary mammary epithelial cells, and post-mitotically terminally differentiated non-replicating cells such as macrophages and/or neurons.

In a preferred embodiment, the cell is a mammalian cell.

In a highly preferred embodiment, the cell is a canine or feline cell.

The term "organism" includes any suitable organism. In a preferred embodiment, the organism is a mammal. In a highly preferred embodiment, the organism is a dog or cat.

Although the 5T4 polypeptide or 5T4-specific agent of the invention may be produced using prokaryotic cells as host cells, it is preferred to use eukaryotic cells, for example yeast, insect or mammalian cells, in particular mammalian cells. Suitable host cells include bacteria such as E. coli, yeast, mammalian cell lines and other eukaryotic cell lines, for example insect Sf9 cells.

The present invention also provides a method comprising transforming a host and/or target cell with a or the nucleotide sequence(s) of the present invention.

The term "transformed cell" means a host cell and/or a target cell having a modified genetic structure. With the present invention, a cell has a modified genetic structure when a vector according to the present invention has been introduced into the cell.

Host cells and/or a target cells may be cultured under suitable conditions which allow expression of the 5T4 polypeptide or 5T4-specific agent of the invention.

The present invention also provides a method comprising culturing a transformed host cell—which cell has been transformed with a or the nucleotide sequence(s) according to the present invention under conditions suitable for the expression of the 5T4 polypeptide or 5T4-specific agent encoded by said nucleotide sequence(s).

The present invention also provides a method comprising culturing a transformed host cell—which cell has been transformed with a or the nucleotide sequence(s) according to the present invention or a derivative, homologue, variant or fragment thereof—under conditions suitable for the expression of the 5T4 polypeptide or 5T4-specific agent encoded by said nucleotide sequence(s); and then recovering said 5T4 polypeptide or 5T4-specific agent from the transformed host cell culture.

The 5T4 polypeptide or 5T4-specific agent of the present invention can be extracted from host cells by a variety of techniques known in the art, including enzymatic, chemical and/or osmotic lysis and physical disruption. The 5T4 polypeptide or 5T4-specific agent may be purified and isolated in a manner known per se.

Regulation of Expression In Vitro/Vivo/Ex Vivo

The present invention also encompasses gene therapy whereby the 5T4 polypeptide or 5T4-specific agent encoding nucleotide sequence(s) of the present invention is regulated in vitro/in vivo/ex vivo. For example, expression regulation may be accomplished by administering compounds that bind to the 5T4 polypeptide or 5T4-specific agent encoding nucleotide sequence(s) of the present invention, or control regions associated with the 5T4 polypeptide or 5T4-specific agent encoding nucleotide sequence of the present invention, or its corresponding RNA transcript to modify the rate of transcription or translation.

Control Sequences

Control sequences operably linked to sequences encoding the 5T4 polypeptide or 5T4-specific agent of the present invention include promoters/enhancers and other expression regulation signals. These control sequences may be selected to be compatible with the host cell and/or target cell in which the expression vector is designed to be used. The control sequences may be modified, for example by the addition of further transcriptional regulatory elements to make the level of transcription directed by the control sequences more responsive to transcriptional modulators.

Operably Linked

The term "operably linked" means that the components described are in a relationship permitting them to function in their intended manner. A regulatory sequence "operably linked" to a coding sequence is ligated in such a way that expression of the coding sequence is achieved under condition compatible with the control sequences.

Preferably the nucleotide sequence of the present invention is operably linked to a transcription unit.

The term "transcription unit(s)" as described herein are regions of nucleic acid containing coding sequences and the signals for achieving expression of those coding sequences independently of any other coding sequences. Thus, each transcription unit generally comprises at least a promoter, an optional enhancer and a polyadenylation signal.

Promoters

The term promoter is well-known in the art and is used to indicate a transcription factor (complex) binding site. The term encompasses nucleic acid regions ranging in size and complexity from minimal promoters to promoters including upstream elements and enhancers.

The promoter is typically selected from promoters which are functional in mammalian, cells, although prokaryotic promoters and promoters functional in other eukaryotic cells may be used. The promoter is typically derived from promoter sequences of viral or eukaryotic genes. For example, it may be a promoter derived from the genome of a cell in which expression is to occur. With respect to eukaryotic promoters, they may be promoters that function, in a ubiquitous manner (such as promoters of α-actin, β-actin, tubulin) or, alternatively, a tissue-specific manner (such as promoters of the genes for pyruvate kinase).

Hypoxic Promoters/Enhancers

The enhancer and/or promoter may be preferentially active in a hypoxic or ischaemic or low glucose environment, such that the 5T4 polypeptide or 5T4-specific agent encoding nucleotide sequence(s) is preferentially expressed in the particular tissues of interest, such as in the environment of a tumor, arthritic joint or other sites of ischaemia, Thus, any significant biological effect or deleterious effect of the 5T4 polypeptide-or 5T4-specific agent encoding nucleotide sequence(s) on the individual being treated may be reduced or eliminated. The enhancer element or other elements conferring regulated expression may be present in multiple copies. Likewise, or in addition, the enhancer and/or promoter may be preferentially active in one or more specific cell types—such as any one or more of macrophages, endothelial cells or combinations thereof. Further examples may include but are not limited to respiratory airway epithelial cells and post-mitotically terminally differentiated non-replicating cells such as macrophages and/or neurons.

Tissue-Specific Promoters

The promoters of the present invention may be tissue-specific promoters. Examples of suitable tissue restricted promoters/enhancers are those which are highly active in tumor cells such as promoter/enhancer from a MUC1 gene, a CEA gene or a 5T4 antigen gene. Examples of temporally restricted promoters/enhancers are those which are responsive to ischaemia and/or hypoxia, such as hypoxia response elements or the promoter/enhancer of grp78 or a grp94 gene. The alpha fetoprotein (AFP) promoter is also tumor-specific promoter. One preferred promoter-enhancer combination is a human cytomegalovirus (hCMV) major immediate early (MIE) promoter/enhancer combination.

Preferably the promoters of the present invention are tissue specific. That is, they are capable of driving transcription of a 5T4 polypeptide or 5T4-specific agent encoding nucleotide sequence(s) in one tissue while remaining largely "silent" in other tissue types.

The term "tissue specific" means a promoter which is not restricted in activity to a single tissue type but which nevertheless shows selectivity in that they may be active in one group of tissues and less active or silent in another group. A desirable characteristic of the promoters of the present invention is that they posses a relatively low activity in the absence of activated hypoxia-regulated enhancer elements, even in the target tissue. One means of achieving this is to use "silencer" elements which suppress the activity of a selected promoter in the absence of hypoxia.

The term "hypoxia" means a condition under which a particular organ or tissue receives an inadequate supply of oxygen.

The level of expression of a or the 5T4 polypeptide or 5T4-specific agent encoding nucleotide sequence(s) under the control of a particular promoter may be modulated by manipulating the promoter region. For example, different domains within a promoter region may possess different gene regulatory activities. The roles of these different regions are typically assessed using vector constructs having different variants of the promoter with specific regions deleted (that is, deletion analysis). This approach may be used to identify, for example, the smallest region capable of conferring tissue specificity or the smallest region conferring hypoxia sensitivity.

A number of tissue specific promoters, described above, may be particularly advantageous in practising the present invention. In most instances, these promoters may be isolated as convenient restriction digestion fragments suitable, for cloning in a selected vector. Alternatively, promoter fragments may be isolated using the polymerase chain reaction. Cloning of the amplified fragments may be facilitated by incorporating restriction sites at the 5' end of the primers.

Inducible Promoters

The promoters of the present invention may also be promoters that respond to specific stimuli, for example promoters that bind steroid hormone receptors. Viral promoters may also be used, for example the Moloney murine leukaemia virus long terminal repeat (MMLV LTR) promoter, the rous sarcoma virus (RSV) LTR promoter or the human cytomegalovirus (CMV) IE promoter.

It may also be advantageous for the promoters to be inducible so that the levels of expression of the heterologous gene can be regulated during the lifetime of the cell. Inducible means that the levels of expression obtained using the promoter can be regulated.

Enhancer

In addition, many of these promoters may be modified by the addition of further regulatory sequences, for example enhancer sequences. Chimeric promoters may also be used comprising sequence elements from two or more different promoters described above.

The term "enhancer" includes a DNA sequence which binds to other protein components of the transcription initiation complex and thus facilitates the initiation of transcription directed by its associated promoter.

The in vitro/in vivo/ex vivo expression of the 5T4 polypeptide or 5T4-specific agent of the present invention may be used in combination with a protein of interest (POI) or a nucleotide sequence of interest (NOI) encoding same.

Combination with POIs/NOIs

The 5T4 polypeptide or 5T4-specific agent of the present invention or nucleotide sequence encoding same may be used in combination with a POI, such as a pro-drug activating enzyme either directly or by vector delivery to, for example, a target cell or target tissue. Instead of or as well as being selectively expressed in target tissues, the 5T4 polypeptide or 5T4-specific agent of the present invention or nucleotide sequence encoding same may be used in combination with another POI such as a pro-drug activation enzyme or enzymes or with nucleotide sequences of interest (NOT) NOIs which encode a pro-drug activation enzyme or enzymes. These pro-drug activation enzyme or enzymes may have no significant effect or no deleterious effect until the individual is treated with one or more pro-drugs upon which the appropriate pro-drug enzyme or enzymes act. In the presence of the active POI or NOIs encoding same, treatment of an individual with the appropriate pro-drug may lead to enhanced reduction in the disease condition such as a reduction in tumor growth or survival.

Pro-Drug POIs

A POI, such as a pro-drug activating enzyme, may be delivered to a disease site, such as a tumor site for the treatment of a cancer. In each case, a suitable pro-drug is used in the treatment of the patient in combination with the appropriate pro-drug activating enzyme. An appropriate pro-drug may be administered in conjunction with the 5T4 polypeptide or 5T4-specific agent or vector comprising the nucleotide sequence encoding same. Examples of pro-drugs include: etoposide phosphate (with alkaline phosphatase, Senter et al. 1988 Proc Natl Acad Sci 85: 4842-4846); 5-fluorocytosine (with cytosine deaminase, Mullen et al. 1994 Cancer Res 54: 1503-1506); Doxorubicin-N-p -hydroxyphenoxyacetamide (with Penicillin-V-Amidase, Kerr et al. 1990 Cancer Immunol Immunother 31: 202-206); Para-N-bis(2-chloroethyl) aminobenzoyl glutamate (with carboxypeptidase G2); Cephalosporin nitrogen mustard carbamates (with.beta.b-lactamase); SR4233 (with P450 Reductase); Ganciclovir (with HSV thymidine kinase, Borrelli et al 1988 Proc Nati Acad Sci 85: 7572-7576); mustard pro-drugs with nitroreductase (Friedlos et al. 1997 J Med. Chem 40: 1270-1275) and Cyclophosphamide (with P450 Chen et al. 1996 Cancer Res 56: 1331-1340).

Examples of suitable pro-drug activation enzymes for use in the invention include a thymidine phosphorylase which activates the 5-fluoro-uracil pro-drugs capcetabine and furtulon; thymidine kinase from Herpes Simplex Virus which activates ganciclovir; a cytochrome P450 which activates a pro-drug such as cyclophosphamide to a DNA damaging agent; and cytosine deaminase which activates 5-fluorocytosine. Preferably, a pro-drug activating enzyme of human origin is used.

POIs and NOIs

Other suitable proteins of interest (POIs) or NOIs encoding same for use in the present invention include those that are of therapeutic and/or diagnostic application such as, but are not limited to: sequences encoding cytokines, chemokines, hormones, antibodies, engineered immunoglobulin-like molecules, a single chain antibody, fusion proteins, enzymes, immune co-stimulatory molecules, immunomodulatory molecules, anti-sense RNA, a transdominant negative mutant of a target protein, a toxin, a conditional toxin, an antigen, a tumor suppressor protein and growth factors, membrane proteins, vasoactive proteins and peptides, anti-viral proteins and ribozymes, and derivatives thereof (such as with an associated reporter group). When included, the POIs or NOIs encoding same may be typically operatively linked to a suitable promoter, which may be a promoter driving expression of a ribozyme(s), or a different promoter or promoters, such as in one or more specific cell types.

Bystander Effect

The POI and/or NOI encoding same may be proteins which are secreted from a cell. Alternatively the POI expression products are not secreted and are active within the cell. In either event, it is preferred for the POI expression product to demonstrate a bystander effector or a distant bystander effect; that is the production of the expression product in one cell leading to the killing of additional, related cells, either neighbouring or distant (e.g. metastatic), which possess a common phenotype.

Suitable POIs or NOIs encoding same for use in the present invention in the treatment or prophylaxis of cancer include proteins which: destroy the target cell (for example a ribosomal toxin), act as: tumor suppressors (such as wild-type p53); activators of anti-tumor immune mechanisms (such as cytokines, co-stimulatory molecules and immunoglobulins); inhibitors of angiogenesis; or which provide enhanced drug sensitivity (such as pro-drug activation enzymes); indirectly stimulate destruction of target cell by natural effector cells (for example, strong antigen to stimulate the immune system or convert a precursor substance to a toxic substance which destroys the target cell (for example a prodrug activating enzyme). Encoded proteins could also destroy bystander tumor cells (for example with secreted antitumor antibody-ribosomal toxin fusion protein), indirectly stimulate destruction of bystander tumor cells (for example cytokines to stimulate the immune system or procoagulant proteins causing local vascular occlusion) or convert a precursor substance to a toxic substance which destroys bystander tumour tumor cells (eg an enzyme which activates a prodrug to a diffusible drug).

Also, the delivery of NOI(s) encoding antisense transcripts or ribozymes which interfere with expression of cellular genes for tumor persistence (for example against aberrant myc transcripts in Burkitts lymphoma or against bcr-abl transcripts in chronic myeloid leukemia. The use of combinations of such POIs and/or NOIs encoding same is also envisaged.

Examples of hypoxia regulatable therapeutic NOIs can be found in PCT/GB95/00322 (WO-A-9521927).

Coupling

The 5T4 polypeptide or 5T4-specific agent of the present invention can be coupled to other molecules using standard methods. The amino and carboxyl termini of 5T4 polypeptide or 5T4-specific agent may be isotopically and nonisotopically labeled with many techniques, for example radiolabeling using conventional techniques (tyrosine residues—chloramine T, iodogen, lactoperoxidase; lysine residues—Bolton-Hunter reagent). These coupling techniques are well known to those skilled in the art. The coupling technique is chosen on the basis of the functional groups available on the amino acids including, but not limited to amino, sulfhydral, carboxyl, amide, phenol, and imidazole. Various reagents used to effect these couplings include among others, glutaraldehyde, diazotized benzidine, carbodiimide, and p-benzoquinone.

Chemical Coupling

The 5T4 polypeptide or 5T4-specific agent of the present invention may be chemically, coupled to isotopes, enzymes, carrier proteins, cytotoxic agents, fluorescent molecules, radioactive nucleotides and other compounds for a variety of applications including but not limited to imaging/prognosis, diagnosis and/or therapy. The efficiency of the coupling reaction is determined using different techniques appropriate for the specific reaction. For example, radiolabeling of an 5T4 polypeptide or 5T4-specific agent peptide with $^{125}$I is accomplished using chloramine T and Na$^{125}$I of high specific activity. The reaction is terminated with sodium metabisulfite and the mixture is desalted on disposable columns. The labeled peptide is eluted from the column and fractions are collected. Aliquots are removed from each fraction and radioactivity measured in a gamma counter. In this manner, the unreacted $Na^{125}I$ is separated from the labeled 5T4 polypeptide or 5T4-specific agent. The peptide fractions with the highest specific radioactivity are stored for subsequent use such as analysis of the ability to bind to a 5T4 polypeptide or 5T4-specific agent.

Imaging

The use of labeled 5T4-specific agents of the present invention with short lived isotopes enables visualization quantitation of 5T4 in vivo using autoradiographie, or modem radiographic or other membrane binding techniques such as positron emission tomography in order to locate tumors with 5T4. This application provides important diagnostic and/or prognostic research tools.

Conjugates

In other embodiments, the 5T4 polypeptide or 5T4-specific agent of the invention is coupled to a scintigraphic radiolabel, a cytotoxic compound or radioisotope, an enzyme for converting a nontoxic prodrug into a cytotoxic drug, a compound for activating the immune system in order to target the resulting conjugate to a disease site such as a colon tumor, or a cell-stimulating compound. Such conjugates have a "binding portion", which consists of the 5T4 polypeptide or 5T4-specific agent of the invention, and a "functional portion", which consists of the radiolabel, toxin or enzyme. Different 5T4 polypeptide or 5T4-specific agents can be synthesized for use in several applications including but not limited to the linkage of a 5T4 polypeptide or 5T4-specific agent to cytotoxic agents for targeted killing of cells that bind the 5T4 polypeptide or 5T4-specific agent.

The binding portion and the functional portion of the conjugate (if also a peptide or polypeptide) may be linked together by any of the conventional ways of cross linking polypeptides, such as those generally described in O'Sullivan et al (Anal. Biochem 1979: 100, 100-108). For example, one portion may be enriched with thiol groups and the other portion reacted with a bifunctional agent capable of reacting with those thiol groups, for example the N-hydroxysuccinimide ester of iodoacetic acid (NHIA) or N-succinimidyl-3-(2-pyridyldithio)propionate (SPDP). Amide and thioether bonds, for example achieved with m-maleimidobenzoyl-N-hydroxysuccinimide ester, are generally more stable in vivo than disulphide bonds.

Alternatively, if the binding portion contains carbohydrates, such as would be the case for an antibody or some antibody fragments, the functional portion may be linked via the carbohydrate portion using the linking technology in EP 0 088 695.

The functional portion of the conjugate may be an enzyme for converting a nontoxic prodrug into a toxic drug, for example the conjugates of Bagshawe and his colleagues (Bagshawe (1987) Br. J. Cancer 56, 531; Bagshawe et al (Br. J. Cancer 1988: 58, 700); WO 88/07378) or cyanide-releasing systems (WO 91/11201).

The conjugate may be purified by size exclusion or affinity chromatography, and tested for dual biological activities. The antigen immunoreactivity may be measured using an enzyme-linked immunosorbent assay (ELISA) with immobilised antigen and in a live cell radio-immunoassay. An enzyme assay may be used for β-glucosidase using a substrate which changes in absorbance when the glucose residues are hydrolysed, such as oNPG (o-nitrophenyl-β-D-glucopyranoside), liberating 2-nitrophenol which is measured spectrophotometrically at 405 nm.

The stability of the conjugate may be tested in vitro initially by incubating at −37° C. in serum, followed by size exclusion FPLC analysis. Stability in vivo can be tested in the same way in mice by analysing the serum at various times after injection of the conjugate. In addition, it is possible to radiolabel the 5T4 polypeptide or 5T4-specific agent with $^{125}I$, and the enzyme with $^{131}I$ before conjugation, and to determine the biodistribution of the conjugate, free 5T4 polypeptide or 5T4-specific agent and free enzyme in mice.

Alternatively, the conjugate may be produced as a fusion compound by recombinant DNA techniques whereby a length of DNA comprises respective regions encoding the two portions of the conjugate either adjacent to one another or separated by a region encoding a linker peptide which does not destroy the desired properties of the conjugate.

Conceivably, two of the functional portions of the compound may overlap wholly or partly. The DNA is then expressed in a suitable host in known ways.

Diagnostic Kits

The present invention also includes diagnostic methods and kits for detection and measurement of 5T4 in biological fluids and tissues, and for localization of 5T4 in tissues. The 5T4 polypeptide or 5T4-specific agent of the present invention that possess high binding specificity can be used to establish easy to use kits for rapid, reliable, sensitive, and specific measurement and localization of a 5T4 in extracts of plasma, urine, tissues, and in cell culture media. The 5T4 polypeptide or 5T4-specific agent of the present invention may also be used in a diagnostic method and kit to permit detection of circulating 5T4 which, in certain situations, may indicate the progression of a disease state such as the spread of micrometastases by primary tumors in situ.

These kits may include but are not limited to the following techniques; competitive and non-competitive assays, radioimmunoassay, bioluminescence and chemiluminescence assays, fluorometric assays, sandwich assays, immunoradiometric assays, dot blots, enzyme linked assays including ELISA, microtiter plates, antibody coated strips or dipsticks for rapid monitoring of urine or blood, and immunocytochemistry. For each kit the range, sensitivity, precision, reliability, specificity and reproducibility of the assay are established. Intraassay and interassay variation is established at 20%, 50% and 80% points on the standard curves of displacement or activity.

One example of an assay kit commonly used in research and in the clinic is a radioimmunoassay (RIA) kit. After successful radioiodination and purification of a 5T4-specific agent, the antiserum possessing the highest titer is added at several dilutions to tubes containing a relatively constant amount of radioactivity, such as 10,000 cpm, in a suitable buffer system. Other tubes contain buffer or preimmune serum to determine the non-specific binding. After incubation at 4° C. for 24 hours, protein A is added and the tubes are vortexed, incubated at room temperature for 90 minutes, and centrifuged at approximately 2000-2500 times g at 4° C. to precipitate the complexes of antiserum bound to the labeled 5T4-specific antibody. The supernatant is removed by aspiration and the radioactivity in the pellets counted in a gamma counter. The antiserum dilution that binds approximately to 40% of the labeled 5T4-specific agent after subtraction of the non-specific binding is further characterized.

Immunohistochemistry

An immunohistochemistry kit may also be used for localization of 5T4 in tissues and cells. This immunohistochemistry kit provides instructions, a 5T4-specific antibody, and possibly blocking serum and secondary antiserum linked to a fluorescent molecule such as fluorescein isothiocyanate, or to some other reagent used to visualize the primary antiserum. Immunohistochemistry techniques are well known to those skilled in the art. This immunohistochemistry kit permits localization of 5T4 in tissue sections and cultured cells using both light and electron microscopy. It is used for both research and clinical purposes. For example, tumors are biopsied or collected and tissue sections cut with a microtome to examine sites of 5T4 production. Such information is useful for diagnostic and possibly therapeutic purposes in the detection and treatment of diseases such as cancer.

Foetal Cell Analysis

The 5T4 polypeptide and 5T4-specific agents of the present invention are also useful in methods for isolating foetal cells from maternal blood. Isolation of foetal cells from maternal blood has been proposed as a noninvasive alternative to aminocentesis (see WO 97/30354).

5T4 is known to be expressed at very high levels on trophoblasts. Thus an antibody against. 5T4 may be used to isolate trophoblasts from maternal blood.

Thus the present invention also provides a method for isolating a foetal cell from maternal blood using an 5T4-specific agent of the present invention The foetal cell may, for example, be a trophoblast or an erythrocyte.

The maternal/foetal cells are preferably from a cat or a dog, such that the isolation method is part of a veterinary application.

The isolation process may form part of a diagnostic method. For example, the foetal cells may then be subject to biochemical or genetic sampling. Such a procedure should be used to test for foetal abnormalities such as Downs syndrome, or to determine the sex of the foetus(es).

Combination Therapy

The 5T4 polypeptide or 5T4-specific agents of the present invention may be used in combination with other compositions and procedures for the treatment of diseases. By way of example, the 5T4 polypeptide or 5T4-specific agents may also be used in combination with conventional treatments of diseases such as cancer. By ways of further example, a tumor may be treated conventionally with surgery, radiation or chemotherapy combined with a 5T4 polypeptide or 5T4-specific agent or a 5T4 polypeptide or 5T4-specific agent may be subsequently administered to the patient to extend the dormancy of micrometastases and to stabilize any residual primary tumor.

Delivery

The 5T4 polypeptide or 5T4-specific agent can be delivered with another therapeutically effective agent at the same moment in time and at the same site. Alternatively, the 5T4 polypeptide or 5T4-specific agent and the therapeutically effective agent may be delivered at a different time and to a different site. The 5T4 polypeptide or 5T4-specific agent and the therapeutically effective agent may even be delivered in the same delivery vehicle for the prevention and/or treatment of a disease condition such as cancer.

Therapeutic strategies based on the use of the 5T4-specific agent include the recruitment and activation of T cells by using a fusion a 5T4-specific agent fragment with the bacterial superantigen staphylococcal enterotoxin (Dohlsten et all 994) or by using bispecific antibodies, directed to both 5T4 and the T-cell CD3 antigen (Kroesen et all 994). Anti-5T4 antibodies may also be conjugated to different bacterial toxins to yield potent immunotoxins (LeMaistre et all 987; Zimmermann et all 997).

5T4 polypeptide or 5T4-specific agents may be used in combination with cytotoxic agents for the prevention and/or treatment of disease states such as angiogenesis and/or cancer. Cytotoxic agents such as ricin, linked to a 5T4-specific agent may provide a tool for the destruction of cells expressing 5T4. These cells may be found in many locations, including but not limited to, micrometastases and primary tumors.

Dosage

The dosage of the composition of the present invention will depend on the disease state or condition being treated and other clinical factors such as weight and condition of the human or animal and the route of administration of the compound. Depending upon the half-life of the active agent in the particular animal or human, the agent (e.g. anti-5T4 antibody) can be administered between several times per day to once a weeks. It is to be understood that the present invention has application primarily for veterinary use. The methods of the present invention contemplate single as well as multiple administrations, given either simultaneously or over an extended period of time.

Formulations

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

The compositions of the present invention may be effective in preventing and/or treating diseases such as cancer related diseases. The present invention includes the method of treating diseases such as cancer related disease with an effective amount of a composition of the present invention. The 5T4 polypeptide or 5T4-specific agent of the present invention can be provided as a synthetic peptide or an isolated and substantially purified proteins or protein fragments or a combination thereof in pharmaceutically acceptable compositions using formulation methods known to those of ordinary skill in the art. These compositions can be administered by standard routes. These include but are not limited to: oral, rectal, ophthalmic (including intravitreal or intracameral), nasal, topical (including buccal and sublingual), intrauterine, vaginal or parenteral (including subcutaneous, intraperitoneal, intramuscular, intravenous, intradefinal, intracranial, intratracheal, and epidural) transdermal, intraperitoneal, intracranial, intracerebroventricular, intracerebral, intravaginal, intrauterine, or parenteral (e.g., intravenous, intraspinal, subcutaneous or intramuscular) routes.

The compositions may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

In addition, the compositions of the present invention may be incorporated into biodegradable polymers allowing for sustained release of the compound, the polymers being implanted in the vicinity of where drug delivery is desired, for example, at the site of a tumor or implanted so that the active agent is slowly released systemically. The biodegradable polymers and their use are described, for example, in detail in Brem et al (J. Neurosurg 1991 74:441-446). Osmotic minipumps may also be used to provide controlled delivery of high concentrations of active agents through cannulae to the site of interest, such as directly into a metastatic growth or into the vascular supply to that tumor.

The 5T4 polypeptide or 5T4-specific agents of the present invention may be linked to cytotoxic agents which are infused in a manner designed to maximize delivery to the desired location. For example, ricin-linked high affinity 5T4 polypeptide or 5T4-specific agents are delivered through a cannula into vessels supplying the target site or directly into the target. Such agents are also delivered in a controlled manner through osmotic pumps coupled to infusion cannulae.

Preferred unit dosage formulations are those containing a daily dose or unit, daily sub-dose, as herein above recited, or an appropriate fraction thereof, of the administered ingredient. It should be understood that in addition to the ingredients, particularly mentioned above, the formulations of the present invention may include other agents conventional in the art having regard to the type of formulation in question.

The conjugates may be administered in any suitable way, usually parenterally, for example intravenously or intraperitoneally, in standard sterile, non-pyrogenic formulations of diluents and carriers, for example isotonic saline (when administered intravenously). Once the conjugate has bound to the target cells and been cleared from the bloodstream (if necessary), which typically takes a day or so, the pro-drug is administered, usually as a single infused dose, or the tumor is imaged. If needed, because the conjugate may be immunogenic, cyclosporin or some other immunosuppressant can be administered to provide a longer period for treatment but usually this will not be necessary.

The timing between administrations of the conjugate and pro-drug may be optimised in a routine way since disease/normal tissue ratios of conjugate (at least following intravenous delivery) are highest after about 4-6 days, whereas at this time the absolute amount of conjugate bound to the 5T4, in terms of percent of injected dose per gram, is lower than at earlier times.

Therefore, the optimum interval between administration of the conjugate and the pro-drug will be a compromise between peak concentration of the enzyme at the disease site and the best distribution ratio between disease and normal tissues. The dosage of the conjugate will be chosen by the physician according to the usual criteria. At last in the case of methods employing a targeted enzyme such as β-glucosidase and intravenous amygdalin as the toxic pro-drug, 1 to 50 daily doses of 0.1 to 10.0 grams per square meter of body surface area, preferably 1.0-5.0 g/m$^2$ are likely to be appropriate. For oral therapy, three doses per day of 0.05 to 1.0.09, preferably 1.0-5.0 g, for one to fifty days may be appropriate. The dosage of the conjugate will similarly be chosen according to normal criteria, particularly with reference to the type, stage and location of the disease tissue and the weight of the patient. The duration of treatment will depend in part upon the rapidity and extent of any immune reaction to the conjugate.

The functional portion of the conjugate, when used for diagnosis, usually comprises and may consist of a radioactive atom for scintigraphic studies, for example technetium 99m ($^{99m}$Tc) or iodine-123 ($^{123}$I), or a spin label for nuclear magnetic resonance (nmr) imaging (also known, as magnetic resonance imaging, mri), such as iodine-123 again, iodine-131, indium-111, fluorine-19, carbon-13, nitrogen-15, oxygen-17, gadolinium, manganese or iron.

When used in a compound for selective destruction of, for example, the tumor, the functional portion of the 5T4-specific agent may comprise a highly radioactive atom, such as iodine-131, rhenium-186, rhenium-188, yttrium-90 or lead-212, which emits enough energy to destroy neighbouring cells, or a cytotoxic chemical compound such as methotrexate, adriamicin, vinca alkaliods (vincristine, vinblastine, etoposide), daunorubicin or other intercalating agents.

The radio- or other labels may be incorporated in the 5T4-specific agent conjugate in known ways. For example, the peptide may be biosynthesised or may be synthesised by chemical amino acid synthesis using suitable amino acid precursors involving, for example, fluorine-19 in place of hydrogen. Labels such as $^{99m}$Tc, $^{123}$I, $^{158}$Rh, $^{188}$Rh and $^{111}$In can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscinigraphy" (Chatal, CRC Press 1989) describes other methods in detail.

Pharmaceutical Compositions

The third aspect of the invention refers to vaccines, priming and boosting compositions, agents and kits. Any and all of the products of this aspect of the invention can be considered to be a pharmaceutical composition.

The pharmaceutical compositions will typically be for animal usage in veterinary medicine and will typically comprise any one or more of a pharmaceutically acceptable diluent, carrier, or excipient. Acceptable carriers or diluents for therapeutic use are well known in the pharmaceutical art, and are described, for example, in Remington's. Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilizers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of, example, the pharmaceutical composition of the present invention may be formulated to be delivered using a minipump or by a mucosal route, for example, as a nasal spray or aerosol for inhalation or ingestible solution, or parenterally in which the composition is formulated by an injectable form, for delivery, by, for example, an intravenous, intramuscular or subcutaneous route. Alternatively, the formulation may be designed to be delivered by both routes.

Where the pharmaceutical composition is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose or chalk, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Administration

Typically, a physician will determine the actual dosage which will be most suitable for an individual subject and it will vary with the age, weight and response of the particular patient and severity of the condition. The dosages below are exemplary of the average case. There can, of course, be individual instances where higher or lower dosage ranges are merited.

The compositions (or component parts thereof) of the present invention may be administered orally. In addition or in the alternative the compositions (or component parts thereof) of the present invention may be administered by direct injection. In addition or in the alternative the compositions (or component parts thereof) of the present invention may be administered topically. In addition or in the alternative the compositions (or component parts thereof) of the present invention may be administered by inhalation. In addition or in the alternative the compositions (or component parts thereof) of the present invention may also be administered by one or more of: parenteral, mucosal, intramuscular, intravenous, subcutaneous, intraocular or transdermal administration means, and are formulated for such administration.

By way of further example, the pharmaceutical composition of the present invention may be administered in accordance with a regimen of 1 to 10 times per day, such as once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The term "administered" also includes but is not limited to delivery by a mucosal route, for example, as a nasal spray or aerosol for inhalation or as an ingestible solution; a parenteral route where delivery is by an injectable form, such as, for example, an intravenous, intramuscular or subcutaneous route.

Hence, the pharmaceutical composition of the present invention may be administered by one or more of the following routes: oral administration, injection (such as direct injection), topical, inhalation, parenteral administration, mucosal administration, intramuscular administration, intravenous administration, subcutaneous administration, intraocular administration or transdermal administration.

Diseases

The present invention provides a method for treating and/or preventing a disease in a subject.

The subject may bit an animal, preferably a companion animal, most preferably a cat or a dog. Preferably the subject is a dog.

The compositions of the invention are contemplated to exhibit therapeutic and/or prophylactic activity, for example, in the treatment and/or prophylaxis of tumors or other diseases associated with cell proliferation, infections and inflammatory conditions. The compositions are particularly effective for cancer immunotherapy.

In particular the compositions are effective for immunotherapy of the feline cancers shown in Table 1 and the canine cancers shown in Table 2. In a highly preferred embodiment there is provided a method for treating and/or preventing a mammary tumor in a dog.

In general the pharmaceutical compositions of the invention may be used in the treatment of disorders such as those listed in WO-A-98/09985.

The invention is further described, for the purposes of illustration only, in the following examples in which reference is made to the following Figures.

FIGURES

FIG. 1 shows human and canine placental sections stained with Y1, an anti-5T4 antibody. A) Human placenta stained with Y1, b) Canine placenta negative control, c) canine placenta stained with Y1

FIG. 3 shows a comparison of feline (SEQ ID NO:3), canine(SEQ ID NO:1), human(SEQ ID NO:12) and murine (SEQ ID NO:11), amino acid sequences.

FIG. 4 shows 293T cells transiently transfected with pIRESneo (A) or pIRES c5T4 (b), formalin fixed and stained with anti-5T4 peptide antiserum.

Figure 6:
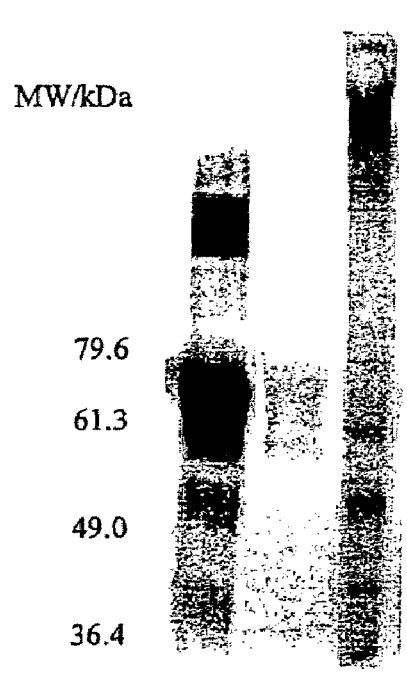

FIG. 6 shows silver staining of c5T4™-EKMycHis.
1. MW marker
2. Purified c5T4™-EKMycHis (1.2 kg for silver stain or 675 ng for western blots
3. MVA-c5T4LacZ-infected CEF cell lysate (cells infected at MOI of 1 and incubated for 24 h)

Figure 7:
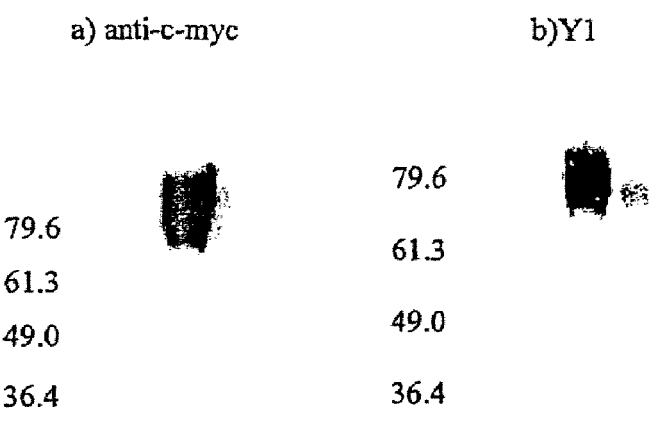

FIG. 7 shows western blotting a) anti-c-myc, b) Y1.

Figure 8:
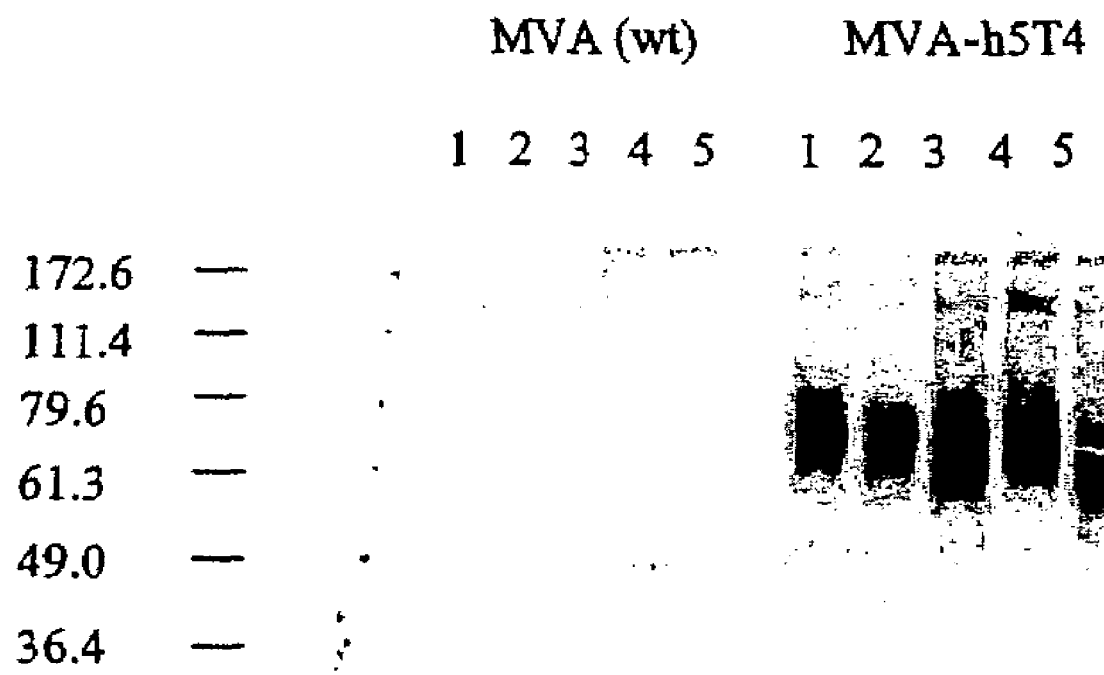

FIG. 8 demonstrates the ability of both canine and feline cells to support expression of 5T4 from recombinant MVA.
1 CF2TH (canine thymus)
2 D17 (poodle osteosarcoma)
3 AKD (foetal feline lung)
4 CRFK (feline kidney)
5 293T (human kidney)

FIG. 9 illustrates cloning c5T-4 into the MVA transfer vectors

FIG. 10 shows CEFs uninfected (panels A and C) and infected with MVA-c5T4lacZ (panels B and D) and immunostained with Y1 (Panels A and B) or Y3-P3 (Panels C and D).

Figure 11:
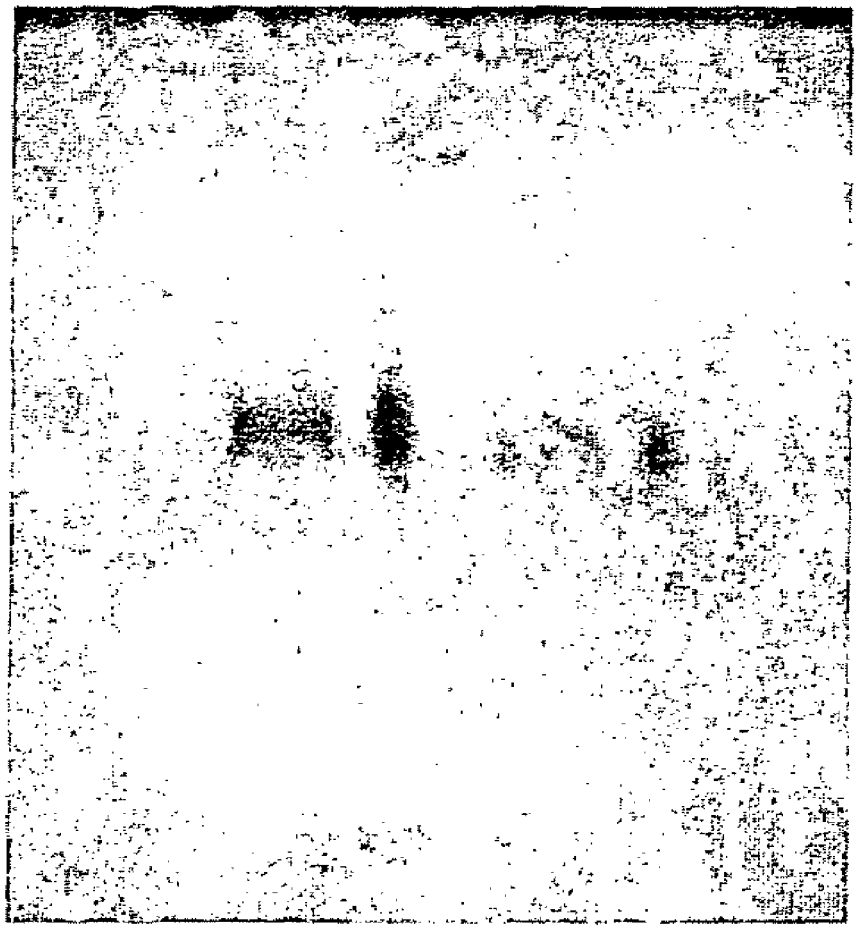

FIG. 11 shows western blotting of lysates from CEFs infected with MVA-c5T4lacZ CEF only
2: MVA_h5T4 (reduced)
3: MVA_h5T4 (unreduced)
4: MVA (wt)
5: MVA-c5T4lacZ (reduced)
6: MVA-c5T4lacZ (unreduced).

Figure 12:

FIG. 12 shows expression of c5T4 in canine thymic cells.
1 CF2TH-MVA-h5T4
2 CF2TH-MVA-c5T4lacZ
3 CF2TH-MVA (wt)

FIG. 13 shows examples of 5T4 positive canine tumor samples. A) mammary carcinoma, B) anal aprocrine carcinoma

EXAMPLES

Example 1

Production of Production of New Anti-5T4 Antibodies

Antibody preparations were raised in chickens against a pool of three, 20 amino acid, 5T4 peptides. Regions that are likely to be surface exposed (hydrophilic), flexible and charged are good candidates for immunogenic peptides. The peptides chosen were as follows:—

```
Pep1
CRYEINADPRLTNLSSNSDV

Pep2
CLNHIVPPEDERQNRSFEG

Pep3
NLSGSRLDEVRAGAFEHLPSLRC
```

One such antiserum, Y1, was demonstrated to recognise both human and canine 5T4, expressed on placenta (FIG. 1)

Y1 antibody preparation was used for most of the analysis of canine and feline tissue samples and in the analysis of 5T4 expressing cell lines and the recombinant MVA.

A concern with Y1 was higher than desired background staining. In an attempt to reduce this, affinity purification was carried out using individual columns of each of the 3 original peptides used in the immunisations. It was demonstrated that the majority of antigenic activity was directed against peptide 3 and so this was used for further purification. The antibody preparation Y3 was successfully purified and significantly improved (see below) using this approach.

Figure 2:
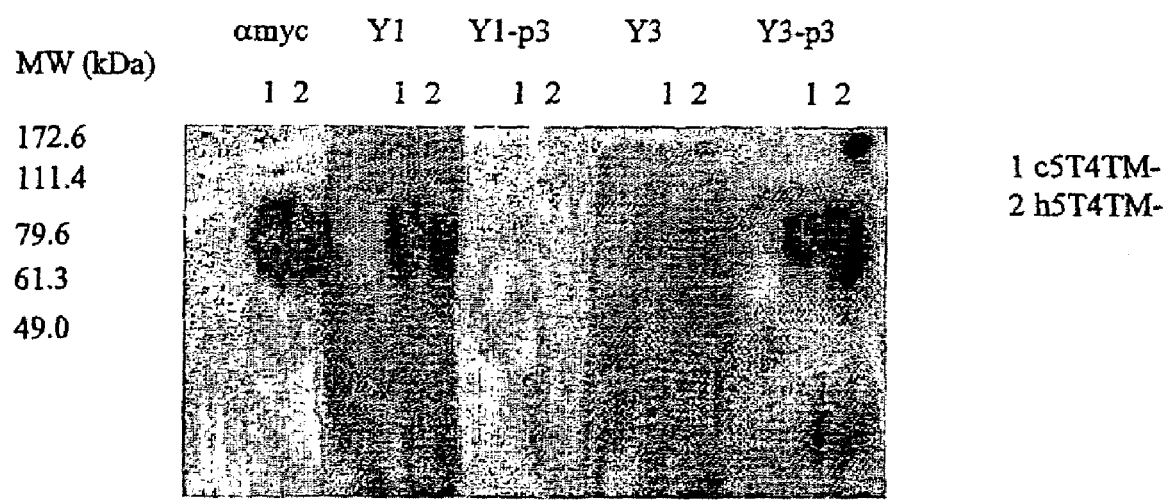
FIG. 2 shows western blotting of truncated human and canin 5T4.

Western blotting of Myc-His tagged, truncated human and canine 5T4 demonstrates that peptide 3 purified Y3 antiserum (Y3-P3) resulted in a high activity anti-5T4 antiserum with low background (FIG. 2). (Conversely, purification of Y1 by this method appeared to result in a loss of activity).

Example 2

Isolation of a Canine and Feline 5T4 Genes

A canine genomic library in λ dash was obtained from Stratagene and screened according to manufacturers instructions using a radiolabelled probe derived from the human 5T4 cDNA. A number of clones were isolated and purified to homogeneity. The gene was identified by southern blot, subcloned into pBSII and sequenced. The canine gene was then used to probe a feline genomic library in the same way and a clone was isolated, subcloned and sequence. A comparison of the feline, canine, human and murine amino acid sequences is shown in FIG. 3.

Cloning into Expression Vectors

The full length c5T4 coding region was amplified by PCR from a pBSII subclone and cloned into the pIRES neo expression vector (Clontech)

293T cells were transfected with pIRES_c5T4, pIRES_h5T4 and pIRES neo. Transfected cells were immunostained with the H8 mAb and the anti 5T4 peptide antiserum, Y1. The Y1 was able to recognise both human and canine 5T4. Transfected cells were also formalin fixed (see FIG. 4).

Example 3

Cloning of Truncated c5T4 with Optimised Kozac Sequence

To produce the c5T4 protein in sufficient quantities for downstream applications such as ELISA, a truncated version of the gene, lacking the transmembrane region and cytoplasmic tail, but tagged c-terminally with a c-myc epitope and 6 histidines (Myc-His), was constructed by PCR to give a secreted protein that could be readily purified from Chinese Hamster Ovary (CHO) cells.

PCR

A 5' primer incorporating a consensus Kozak sequence was used in conjunction with a 3' primer situated immediately upstream of the transmembrane region to amplify the truncated cDNA. This product was then spliced into a pGEM-TEasy vector containing an Enterokinase cleavage site N-terminal to a Myc-His tag. The truncated c5T4_EKMycHis was then cloned into pIRES neo.

This construct (pIRES_c5T4 Tm-) was transfected into CHO cells and stable lines made using G418 selection. Clones expressing the c5T4_EKMycHis were assessed by immunostaining with the Y1 chicken antiserum and an anti-His antibody.

Figure 5:
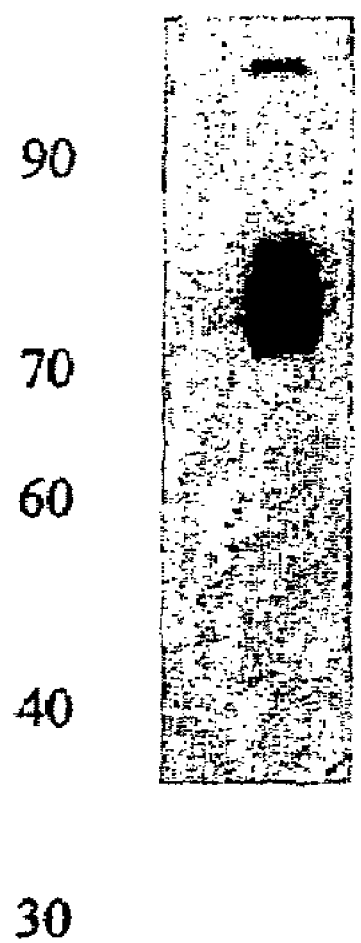
FIG. 5 shows western blotting of cell supernatants to demonstrate the presence of a pIRES_c5T4 TM-stable transfectant.

Western blotting of cell supernatants with an anti-Myc antibody demonstrates the presence of 5T4 in the cell supernatants of a pIRES_c5T4 TM-stable transfectant (FIG. 5).

A suitable done was then expanded and the supernatant harvested. The c5T4_EKMycHis protein was then isolated on a nickel column and purity assessed by PAGE followed by coomassie staining and western blot analysis.

Purification of c5T4TM-EKMycHis c5T4TM-EKMycHis was double-purified from 1 1 CHO-c5T4TM-EKMycHis supernatant cells using a 5 ml HiTrap Chelating column and associated HisTrap kit (Amersham Pharmacia Biotech) and the imidazole concentration from elution was reduced by dialysis against 1×PBS (FIG. 6).

Example 4

Cloning Feline 5T4

The feline 5T4 gene was isolated from a feline genomic lambda library, and following restriction analysis and Southern blotting, a 3 kb DNA fragment was cloned into pBluescript (Stratagene) and sequenced—found to contain f5T4 gene. This was then amplified by PCR to clone both full-length and TM-f5T4 into expression vectors (pIRESneo) for transfection into CHO cells. The feline gene has also been cloned into the appropriate MVA transfer plasmids in order to make recombinant MVA_f5T4.

Analysis of cloned cell line CHO-f5T4tm- reveals immunostaining identical to that of CHO-c5T4tm-.

Example 5

Production of Recombinant MVA_c5T4

The canin 5T4 gene was cloned into the MVA vector and expression of the canine 5T4 protein in cells infected with the modified virus was demonstrated. Expression of the canine protein in canine thymic cells was also demonstrated and a stock of MVA_c54 vaccine prepared.

To demonstrate the ability of both feline and canine cells to support expression of 5T4 from recombinant MVA, western blot analysis of the following cells; C2fTH (Canine thymus), D17 (Poodle osteosarcoma), AK-D (Feline Foetal lung), CRFK (Feline Kidney), infected with recombinant MVA_h5T4 was carried out. The cells were infected with MVA or MVA/h5T4 at an MOI of 5 and then harvested 24 hours later. Lysates were subjected to PAGE and electroblotting to Hybond ECL and 5T4 was then detected with mAb H8 followed by RαM-HRP and ECL (FIG. 8).

Example 6

Cloning c5T4 into the MVA Transfer Vectors

Methods for propagation of MVA, preparation of CEF cells and homologous recombination are described in WO 00/29428.

The full length c5T4 cDNA, amplified by PCR, was cloned into an MVA transfer plasmid with the LacZ marker gene (FIG. 9) which was then used to make recombinant MVA_c5T4_LacZ by cotransfection with MVA into CEFs. The recombinant virus has been purified to homogeneity through 4 rounds of plaque picking, with no background of wild type virus detected. Immunostaining of infected CEF cells with the Y1 chicken antiserum confirmed the presence of 5T4 in the virus and PCR amplification of a ~350 bp fragment of 5T4 sequence from viral DNA has confirmed the 5T4 gene as canine.

Example 7

Induction of c5T4 Expression in CEFs and Canine Thymic Cells

Canine 5T4 was expressed in CEFs infected with recombinant MVA 5T4. CEFs infected with MVA-c5T4lacZ (MOI=0.02) were immunostained with Y1 and Y3-P3 (FIG. 10) showing c5T4 expression.

Lysates from CEFs infected with MVA-c5T4lacZ (MOI=1) were analysed by Western Blot using Y1 (FIG. 11).

Having shown that the recombinant MVA_c5T4 expresses 5T4 protein in CEFs it was also demonstrated that the protein could be expressed in canine cells. FIG. 12 shows a Western Blot of canine thymic (CF2TH) cells infected by MVA_c5T4lacZ and MVA_h5T4, detected using Y1.

Example 8

Immunohistochemistry of Canine and Feline Tissues

Normal canine tissues have been stained for 5T4 using the Y1 antiserum, as shown below:

| Tissue | No. Positive |
|---|---|
| Brain | 0/3 |
| Cerebellum | 0/3 |
| Heart | 0/3 |
| Lung | 1/3 |
| Liver | 2/3 |
| Kidney | 3/3 |
| Pituitary | 3/3 |

The positive samples may be due to 5T4 expression but could be due to some cross reactivity of Y1. To address the later possibility, the purified Y3-P3 has been used to repeat these studies of normal tissues. To date only some specific cells of the pituitary have stained positive with Y3-P3 whilst the cancer tissue samples that have been stained with this antisera have remained positive.

A summary of the Y1 staining of canine and feline cancer samples are given in tables 1 & 2. Out of all the different feline tumor types studied 23% (6/26) were positive. This rises to 38% (3/8) for mammary tumors only. The percentage of 5T4 positive tumors is higher in the canine samples; 45% (30/66) for all types. When mammary tumors, which make up 42% of all the tumors types presented to Oncodesign, are analysed separately, 75% (21/28) are 5T4 positive.

FIG. 13 shows two examples of 5T4 positive canine tumor samples: mammary carcinoma (A) and anal apocrine carcinoma (B)

TABLE 1

| FELINE SAMPLES | | | | |
|---|---|---|---|---|
| | Sex | N°. +ve | N°. −ve | % +ve |
| Mammary Tumours:- | | | | |
| Adenocarcinoma | M | | | |
| | F | 2 | 4 | 33 |
| Lymphoma | M | | | |
| | F | | 1 | 0 |
| Recurrence of canalicular(?) | M | | | |
| | F | 1 | | 100 |
| TOTAL Mammary | M | — | — | |
| | F | 3 | 5 | 38 |
| Intra muscular fibromatosis | M | | | |
| | F | 1 | | 100 |
| Malignant Fibroblast | M | | | |
| | F | | 1 | 0 |
| Bladder carcinoma | M | | | |
| | F | 1 | | 100 |
| Sarcoma | M | | | |
| | F | | 1 | 0 |
| Fibrosarcoma | M | | 2 | 0 |
| | F | | 6 | 0 |
| Fibrohistocytoma | M | | 1 | 0 |
| | F | | 4 | |
| ALL CANCERS (n = 26) | M | | 3 | 0 |
| | F | 6 | 17 | 26 |
| | Both | 6 | 20 | 23 |

TABLE 2

CANINE SAMPLES

| | Sex | N°⋅ +ve | N°⋅ −ve | % +ve |
|---|---|---|---|---|
| Mammary Tumours:- | | | | |
| (Adeno)carcinoma | M | | | |
| | F | 15 | 3 | 83 |
| Epithelial | M | | | |
| | F | 5 | 1 | 83 |
| Mesenchymal | M | | | |
| | F | | 1 | 0 |
| Intracanalicular(?) | M | | | |
| | F | 1 | | 100 |
| Sarcoma | M | | | |
| | F | | 1 | 0 |
| Cutaneous Metastasis | M | | | |
| | F | | 1 | 0 |
| TOTAL | M | | | |
| | F | 21 | 7 | 75 |
| Anal apocrine gland (+met.) | M | | 1 | 0 |
| | F | 1 | | 100 |
| Intestinal Adenocarcinoma | M | | | |
| | F | 1 | | 100 |
| Pre-cancerous mastopathy | M | | | |
| | F | 2 | 1 | 67 |
| Epidermoid Carcinoma | M | 1 | | 100 |
| | F | 1 | | 100 |
| Dermo-epidermic lesion | M | | | |
| | F | 1 | | 100 |
| Mast cell cancers | M | | 3 | 0 |
| | F | | 2 | 0 |
| Bladder carcinoma | M | | | |
| | F | 1 | 1 | 50 |
| Osteosarcoma | M | 1 | | 100 |
| | F | | | |
| Hepatocarcinoma | M | | 1 | 0 |
| | F | | | |
| Seminoma | M | | 2 | 0 |
| | F | | | |
| Thyroid Carcinoma | M | | | |
| | F | | 1 | 0 |
| Lymphoma | M | | 2 | 0 |
| | F | | 1 | 0 |
| Myxosarcoma | M | | 1 | 0 |
| | F | | | |
| Fibrosarcoma | M | | 1 | 0 |
| | F | | | |
| Fibrohistocytoma | M | | | |
| | F | | 1 | 0 |
| Rhabdomyosarcoma | M | | | |
| | F | | 1 | 0 |
| Malignant melanoma | M | | 5 | 0 |
| | F | | | |
| Malignant scwannoma | M | | | |
| | F | | 1 | 0 |
| Hemangiopericytoma | M | | 1 | 0 |
| | F | | 2 | 0 |
| Sertolinoma | M | | 1 | 0 |
| | F | | | |
| ALL CANCERS (n = 66) | M | 2 | 18 | 10 |
| | F | 28 | 18 | 61 |
| | Both | 30 | 36 | 45 |

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:

1. An isolated nucleotide sequence which encodes the feline 5T4 polypeptide set forth in SEQ ID NO: 3.

2. The nucleotide sequence of claim 1 having the sequence set forth in SEQ ID NO: 4.

3. A vector comprising the nucleotide sequence of claim 1.

4. The vector of claim 3, wherein the vector is a Modified Vaccinia Ankara (MVA) vector.

5. A kit which comprises:
(a) a first composition comprising a nucleotide sequence encoding a feline 5T4 antigen, and
(b) a second composition comprising the vector of claim 3 for simultaneous, separate or sequential administration to a subject.

6. The kit of claim 5, wherein the first composition comprises a nucleotide sequence encoding a feline 5T4 antigen, wherein the antigen has the amino acid sequence set forth in SEQ ID NO: 3.

* * * * *

UNITED STATES PATENT AND TRADEMARK OFFICE
CERTIFICATE OF CORRECTION

PATENT NO.        : 7,659,383 B2                                    Page 1 of 1
APPLICATION NO. : 12/169222
DATED             : February 9, 2010
INVENTOR(S)       : Kevin A. Myers et al.

It is certified that error appears in the above-identified patent and that said Letters Patent is hereby corrected as shown below:

At column 2, lines 37-41, please delete "Thus, the invention provides a kit comprising a vector according to the second aspect of the invention and an agent according to the third aspect of the invention, for simultaneous, separate, or sequential use, preferably for use in the treatment of tumours." and insert --The present invention also provides to the sequential use of a vector encoding a 5T4 antigen and such an anti-5T4 agent. Where the anti-5T4 agent is a protein (such as an antibody or derivative thereof) it may be administered as naked DNA (for example, in a plasmid), or in an expression vector (which may be viral or non-viral) or directly in a protein form. The agent may be fused with an immunostimulatory molecule.--

At column 2, line 53, please delete "that" and insert --than--

At column 6, line 24, please delete "canin" and insert --canine--

At column 6, line 25, please delete "felin" and insert --feline--

At column 6, line 52, please delete "Hybridisation" and insert --Hybridization--

At column 11, line 63, please delete "bee" and insert --be--

At column 12, line 62, please delete "lentivirus s" and insert --lentiviruses--

At column 20, line 29, please delete "tumour tumour" and insert --tumour--

At column 20, line 58, please delete "chemically," and insert --chemically--

At column 24, line 17, please delete "weeks" and insert --week--

At column 28, line 24, please delete "canin" and insert --canine--

At column 31, line 5, please delete "canin" and insert --canine--

Signed and Sealed this

Twenty-fourth Day of August, 2010

David J. Kappos
*Director of the United States Patent and Trademark Office*

```
                        SEQUENCE LISTING

<160> NUMBER OF SEQ ID NOS: 12

<210> SEQ ID NO 1
<211> LENGTH: 420
<212> TYPE: PRT
<213> ORGANISM: Canis sp.

<400> SEQUENCE: 1

Met Pro Gly Gly Cys Ser Arg Gly Pro Ala Ala Gly Asp Gly Arg Leu
1               5                   10                  15

Arg Leu Ala Arg Leu Ala Leu Val Leu Leu Gly Trp Val Ser Ser Ser
            20                  25                  30

Ser Leu Thr Ser Trp Ala Pro Ser Ala Ala Ala Ser Thr Ser Pro Pro
        35                  40                  45

Ala Ser Ala Ala Ser Ala Pro Pro Leu Pro Gly Gln Cys Pro Gln
    50                  55                  60

Pro Cys Glu Cys Ser Glu Ala Ala Arg Thr Val Lys Cys Val Asn Arg
65                  70                  75                  80

Asn Leu Thr Glu Val Pro Ala Asp Leu Pro Pro Tyr Val Arg Asn Leu
                85                  90                  95
```

```
Phe Leu Thr Gly Asn Gln Leu Ala Val Leu Pro Pro Gly Ala Phe Ala
            100                 105                 110

Arg Arg Pro Pro Leu Ala Glu Leu Ala Ala Leu Asn Leu Ser Gly Ser
        115                 120                 125

Ser Leu Arg Glu Val Cys Ala Gly Ala Phe Glu His Leu Pro Ser Leu
    130                 135                 140

Arg Gln Leu Asp Leu Ser His Asn Pro Leu Gly Asn Leu Ser Ala Phe
145                 150                 155                 160

Ala Phe Ala Gly Ser Asp Ala Ser Arg Ser Gly Pro Ser Pro Leu Val
                165                 170                 175

Glu Leu Met Leu Asn His Ile Val Pro Pro Asp Arg Arg Gln Asn
            180                 185                 190

Arg Ser Phe Glu Gly Met Val Ala Ala Leu Arg Ala Gly Arg Ala
        195                 200                 205

Leu Arg Gly Leu Gln Cys Leu Glu Leu Ala Gly Asn Arg Phe Leu Tyr
    210                 215                 220

Leu Pro Arg Asp Val Leu Ala Gln Leu Pro Gly Leu Arg His Leu Asp
225                 230                 235                 240

Leu Arg Asn Asn Ser Leu Val Ser Leu Thr Tyr Val Ser Phe Arg Asn
                245                 250                 255

Leu Thr His Leu Glu Ser Leu His Leu Glu Asp Asn Ala Leu Lys Val
            260                 265                 270

Leu His Asn Ala Thr Leu Ala Glu Leu Gln Ser Leu Pro His Val Arg
        275                 280                 285

Val Phe Leu Asp Asn Asn Pro Trp Val Cys Asp Cys His Met Ala Asp
    290                 295                 300

Met Val Ala Trp Leu Lys Glu Thr Glu Val Val Pro Gly Lys Ala Gly
305                 310                 315                 320

Leu Thr Cys Ala Phe Pro Glu Lys Met Arg Asn Arg Ala Leu Leu Glu
                325                 330                 335

Leu Asn Ser Ser His Leu Asp Cys Asp Pro Ile Leu Pro Pro Ser Leu
            340                 345                 350

Gln Thr Ser Tyr Val Phe Leu Gly Ile Val Leu Ala Leu Ile Gly Ala
        355                 360                 365

Ile Phe Leu Leu Val Leu Tyr Leu Asn Arg Lys Gly Ile Lys Lys Trp
    370                 375                 380

Met His Asn Ile Arg Asp Ala Cys Arg Asp His Met Glu Gly Tyr His
385                 390                 395                 400

Tyr Arg Tyr Glu Ile Asn Ala Asp Pro Arg Leu Thr Asn Leu Ser Ser
                405                 410                 415

Asn Ser Asp Val
            420

<210> SEQ ID NO 2
<211> LENGTH: 1263
<212> TYPE: DNA
<213> ORGANISM: Canis sp.

<400> SEQUENCE: 2
atgcctgggg ggtgctcccg gggccccgcc gccggggacg ggcggttgcg gctggcgcgg      60
ctggcgctgg tgctcctggg ctgggtctcc tcgtcctcgc tcacctcctg ggcgccctcc     120
gccgccgcct ccacgtcgcc gccggcctcc ggggcgtccg cccgccccc gctgccgggc      180 cagtgccccc agccttgcga gtgctcggag gcggcgcgca cggtcaagtg cgttaaccgc     240
```

```
aacctgaccg aggtgcccgc ggacctgccc ccctacgtgc gcaacctctt cctcacgggc    300
aaccagctgg cggtgctgcc ccccggcgcc ttcgcccgcc ggccgccgct ggccgagctg    360
gccgcgctca acctgagcgg cagcagcctg cgggaggtgt gcgccggcgc cttcgagcac    420
ctgcccagcc tgcgccagct cgacctcagc cacaacccgc tgggcaacct cagcgccttc    480
gccttcgcgg gcagcgacgc cagccgctcg ggccccagcc ccctggtgga gctgatgctg    540
aaccacatcg tgcccccga cgaccggcgg cagaaccgga gcttcgaggg catggtggcg    600
gctgccctcc gagcgggccg ccgcgcttcg gggctgcagt gcctggagct ggccggcaac    660
cgcttcctct acttgcctcg cgacgtcctg cccagctac ccggcctccg gcacctggac    720
ctgcgcaaca actccctggt gagcctcacc tacgtgtcct tccgcaacct gacgcacttg    780
gagagcctcc acctggagga caacgccctc aaggtccttc acaacgccac cctggcggag    840
ctgcagagcc tgccccacgt ccgggtcttc ctggacaaca cccctgggt ctgcgattgt    900 cacatggcag acatggtggc ctggctcaag gagacagagg tggtgccggg caaagccggg    960
ctcacctgtg cattcccgga gaaaatgagg aatcgggccc tcttggaact caacagctcc   1020
cacctggact gtgaccctat cctcccctcca tccctgcaga cttcttatgt cttcctaggt   1080
attgtcttag ccctgatagg cgccatcttc ctactggttt tgtatttgaa ccgcaagggg   1140
ataaagaagt ggatgcataa catcagagat gcctgcaggg atcacatgga agggtatcac   1200
tacagatacg aaatcaatgc agaccccagg ttaacaaacc tcagttccaa ttcggatgtc   1260
tga                                                                 1263

<210> SEQ ID NO 3
<211> LENGTH: 419
<212> TYPE: PRT
<213> ORGANISM: Felis sp.

<400> SEQUENCE: 3

Met Pro Gly Gly Cys Ser Arg Gly Pro Ala Ala Gly Asp Gly Arg Leu
1               5                   10                  15

Arg Leu Ala Arg Leu Ala Leu Val Leu Leu Gly Trp Val Ser Ser Ser
            20                  25                  30

Ser Leu Thr Ser Ser Ala Pro Ser Thr Ser Ser Thr Ser Phe Leu Ala
        35                  40                  45

Ser Ala Val Ser Ala Gln Pro Pro Leu Pro Gly Gln Cys Pro Gln Leu
    50                  55                  60

Cys Glu Cys Ser Glu Ala Ala Arg Thr Val Lys Cys Val Asn Arg Asn
65                  70                  75                  80

Leu Thr Glu Val Pro Ala Asp Leu Pro Pro Tyr Val Arg Asn Leu Phe
                85                  90                  95

Leu Thr Gly Asn Gln Leu Ala Val Leu Pro Ala Gly Ala Phe Ala Arg
            100                 105                 110

Arg Pro Pro Leu Ala Glu Leu Ala Ala Leu Asn Leu Ser Gly Ser Arg
        115                 120                 125

Leu Gln Glu Val Arg Ala Gly Ala Phe Glu Gln Leu Pro Ser Leu Arg
    130                 135                 140

Gln Leu Asp Leu Ser His Asn Pro Leu Ala His Leu Ser Pro Phe Thr
145                 150                 155                 160

Phe Ser Gly Ser Asn Ala Ser Phe Ser Ala Pro Ser Pro Leu Val Glu
                165                 170                 175

Leu Met Leu Asn His Ile Val Pro Pro Glu Asp His Arg His Asn Arg
            180                 185                 190
```

Ser Phe Glu Gly Met Val Ala Ala Ser Leu Arg Ala Gly His Ala Leu
            195                 200                 205

Arg Gly Leu Gln Arg Leu Glu Leu Ala Ser Asn His Phe Leu Phe Leu
        210                 215                 220

Pro Arg Asp Val Leu Ala His Leu Pro Gly Leu Arg His Leu Asp Leu
225                 230                 235                 240

Arg Asn Asn Ser Leu Val Ser Leu Thr Tyr Val Ser Phe Arg Asn Leu
                245                 250                 255

Thr His Leu Gln Ser Leu His Leu Glu Asp Asn Ala Leu Lys Val Leu
            260                 265                 270

His Asn Gly Thr Met Ala Glu Leu Gln Ser Leu Pro His Val Arg Val
        275                 280                 285

Phe Leu Asp Asn Asn Pro Trp Val Cys Asp Cys His Met Val Asp Met
    290                 295                 300

Val Ala Trp Leu Lys Glu Thr Glu Val Val Gln Gly Lys Ala Arg Leu
305                 310                 315                 320

Ala Cys Ala Phe Pro Glu Lys Met Arg Asn Arg Ala Leu Leu Glu Leu
                325                 330                 335

Asn Ser Ser His Leu Glu Cys Asp Pro Ile Leu Pro Pro Ser Leu Gln
            340                 345                 350

Thr Ser Tyr Val Phe Leu Gly Ile Val Leu Ala Leu Ile Gly Ala Ile
        355                 360                 365

Phe Leu Leu Val Leu Tyr Leu Asn Arg Lys Gly Ile Lys Lys Trp Met
    370                 375                 380

His Asn Ile Arg Asp Ala Cys Arg Asp His Met Glu Gly Tyr His Tyr
385                 390                 395                 400

Arg Tyr Glu Ile Asn Ala Asp Pro Arg Leu Thr Asn Leu Ser Ser Asn
                405                 410                 415

Ser Asp Val

<210> SEQ ID NO 4
<211> LENGTH: 1260
<212> TYPE: DNA
<213> ORGANISM: Felis sp.

<400> SEQUENCE: 4

| | | |
|---|---|---|
| atgcctgggg ggtgctcccg gggccccgcc gccggagacg gcggctgcg gctggcgcgg | 60 |
| ctggcgctgg tcctcctggg ctgggtctct tcgtcttctc tcacttcctc ggcgccctcc | 120 |
| acctcctcca cgtcgttcct ggcctccgcg gtgtccgccc agcccccgct gccgggccaa | 180 |
| tgccccagc tttgcgagtg ctccgaggcg cgcgcactg tcaagtgcgt taaccgcaac | 240 |
| ctgaccgagg tgcccgcgga cctgcccccc tacgtgcgca acctcttcct caccggcaat | 300 |
| cagctggccg tgctccccgc cggcgccttc gcccgccggc cgccgctggc ggagctggcc | 360 |
| gcgctcaacc tcagcggcag ccgcctgcag gaggtgcgcg ccggcgcctt cgagcaactg | 420 |
| cccagcctgc ggcagctcga cctcagccac aacccgctgg cccacctcag ccccttcacc | 480 |
| ttctcgggca gcaacgccag cttctcggcc ccagcccccc tggtggaact gatgctgaac | 540 |
| cacatcgtgc ccctgaggac caccggcac aaccggagct cgagggtat ggtgcggcg | 600 |
| tccctacgcg ccgccatgc gcttcgcggg ctccagcgcc tygaactggc cagcaaccac | 660 |
| ttcctcttct tgcctcggga cgtactggcc cacctaccgg gcctcaggca cctggacctg | 720 |
| cgcaacaact cgctggtgag cctaacttac gtgtccttcc gcaacctgac acacctacaa | 780 |

-continued

```
agcctccacc tggaggacaa cgccctcaag gtccttcaca acggcaccat ggcggagttg      840
cagagcctgc cccacgtcag ggtcttcctg acaacaatc cctgggtctg cgactgtcac       900
atggtggaca tggtggcctg gctcaaggag acagaggtag tgcagggcaa agccaggctc      960
gcctgtgcat tcccggaaaa aatgaggaat cgggccctt tggaactcaa cagctcccac      1020
ctggagtgtg accctatcct ccctccatcc ctgcagactt cttatgtctt tctaggtatt     1080
gttttagccc tgataggtgc cattttctta ctggttttgt acttgaaccg caaggggata     1140
aaaaagtgga tgcataacat cagagatgcc tgcagggatc acatggaagg gtatcactac     1200
agatatgaaa tcaacgcgga ccccaggtta acaaacctca gttctaattc ggatgtctga     1260
```

<210> SEQ ID NO 5
<211> LENGTH: 34
<212> TYPE: DNA
<213> ORGANISM: Canis sp.

<400> SEQUENCE: 5
cccagctccg ggagcgccgc gccgcgccgc gatg                                  34

<210> SEQ ID NO 6
<211> LENGTH: 21
<212> TYPE: DNA
<213> ORGANISM: Homo sapiens

<400> SEQUENCE: 6
agctccgggg aaacgcgagc c                                                21

<210> SEQ ID NO 7
<211> LENGTH: 30
<212> TYPE: DNA
<213> ORGANISM: Homo sapiens

<400> SEQUENCE: 7
cccagctccg gggaaacgcg agccgcgatg                                       30

<210> SEQ ID NO 8
<211> LENGTH: 20
<212> TYPE: PRT
<213> ORGANISM: Artificial sequence
<220> FEATURE:
<223> OTHER INFORMATION: 5T4 peptide for antibody production, described
      in Example 1

<400> SEQUENCE: 8

Cys Arg Tyr Glu Ile Asn Ala Asp Pro Arg Leu Thr Asn Leu Ser Ser
1               5                   10                  15

Asn Ser Asp Val
            20

<210> SEQ ID NO 9
<211> LENGTH: 19
<212> TYPE: PRT
<213> ORGANISM: Artificial sequence
<220> FEATURE:
<223> OTHER INFORMATION: 5T4 peptide for antibody production, described
      in Example 1

<400> SEQUENCE: 9

Cys Leu Asn His Ile Val Pro Pro Glu Asp Glu Arg Gln Asn Arg Ser
1               5                   10                  15

Phe Glu Gly

```
<210> SEQ ID NO 10
<211> LENGTH: 23
<212> TYPE: PRT
<213> ORGANISM: Artificial sequence
<220> FEATURE:
<223> OTHER INFORMATION: 5T4 peptide for antibody production, described
      in Example 1

<400> SEQUENCE: 10

Asn Leu Ser Gly Ser Arg Leu Asp Glu Val Arg Ala Gly Ala Phe Glu
1               5                   10                  15

His Leu Pro Ser Leu Arg Cys
            20

<210> SEQ ID NO 11
<211> LENGTH: 426
<212> TYPE: PRT
<213> ORGANISM: Mus sp.

<400> SEQUENCE: 11

Met Pro Gly Ala Gly Ser Arg Gly Pro Ser Ala Gly Asp Gly Arg Leu
1               5                   10                  15

Arg Leu Ala Arg Leu Ala Leu Val Leu Leu Gly Trp Val Ser Ala Ser
                20                  25                  30

Ala Pro Ser Ser Val Pro Ser Ser Thr Ser Pro Ala Asp Phe
            35                  40                  45

Leu Ala Ser Gly Ser Ala Gln Pro Pro Ala Glu Arg Cys Pro Ala
    50                  55                  60

Ala Cys Glu Cys Ser Glu Ala Ala Arg Thr Val Lys Cys Val Asn Arg
65                  70                  75                  80

Asn Leu Leu Glu Val Pro Ala Asp Leu Pro Pro Tyr Val Arg Asn Leu
                85                  90                  95

Phe Leu Thr Gly Asn Gln Met Thr Val Leu Pro Ala Gly Ala Phe Ala
                100                 105                 110

Arg Gln Pro Pro Leu Ala Asp Leu Glu Ala Leu Asn Leu Ser Gly Asn
            115                 120                 125

His Leu Lys Glu Val Cys Ala Gly Ala Phe Glu His Leu Pro Gly Leu
    130                 135                 140

Arg Arg Leu Asp Leu Ser His Asn Pro Leu Thr Asn Leu Ser Ala Phe
145                 150                 155                 160

Val Phe Ala Gly Ser Asn Ala Ser Val Ser Ala Pro Ser Pro Leu Glu
                165                 170                 175

Glu Leu Ile Leu Asn His Ile Val Pro Pro Glu Asp Gln Arg Gln Asn
                180                 185                 190

Gly Ser Phe Glu Gly Met Val Ala Phe Glu Gly Met Val Ala Ala Ala
            195                 200                 205

Leu Arg Ser Gly Leu Ala Leu Arg Gly Leu Thr Arg Leu Glu Leu Ala
    210                 215                 220

Ser Asn His Phe Leu Phe Leu Pro Arg Asp Leu Leu Ala Gln Leu Pro
225                 230                 235                 240

Ser Leu Arg Tyr Leu Asp Leu Arg Asn Asn Ser Leu Val Ser Leu Thr
                245                 250                 255

Tyr Ala Ser Phe Arg Asn Leu Thr His Leu Glu Ser Leu His Leu Glu
                260                 265                 270

Asp Asn Ala Leu Lys Val Leu His Asn Ser Thr Leu Ala Glu Trp Gln
            275                 280                 285
```

-continued

```
Gly Leu Ala His Val Lys Val Phe Leu Asp Asn Asn Pro Trp Val Cys
        290                 295                 300

Asp Cys Tyr Met Ala Asp Met Val Ala Trp Leu Lys Glu Thr Glu Val
305                 310                 315                 320

Val Pro Asp Lys Ala Arg Leu Thr Cys Ala Phe Pro Glu Lys Met Arg
                325                 330                 335

Asn Arg Gly Leu Leu Asp Leu Asn Ser Ser Asp Leu Asp Cys Asp Ala
                340                 345                 350

Val Leu Pro Gln Ser Leu Gln Thr Ser Tyr Val Phe Leu Gly Ile Val
                355                 360                 365

Leu Ala Leu Ile Gly Ala Ile Phe Leu Leu Val Leu Tyr Leu Asn Arg
        370                 375                 380

Lys Gly Ile Lys Lys Trp Met His Asn Ile Arg Asp Ala Cys Arg Asp
385                 390                 395                 400

His Met Glu Gly Tyr His Tyr Arg Tyr Glu Ile Asn Ala Asp Pro Arg
                405                 410                 415

Leu Thr Asn Leu Ser Ser Asn Ser Asp Val
                420                 425

<210> SEQ ID NO 12
<211> LENGTH: 420
<212> TYPE: PRT
<213> ORGANISM: Homo sapiens

<400> SEQUENCE: 12

Met Pro Gly Gly Cys Ser Arg Gly Pro Ala Ala Gly Asp Gly Arg Leu
1               5                   10                  15

Arg Leu Ala Arg Leu Ala Leu Val Leu Leu Gly Trp Val Ser Ser Ser
            20                  25                  30

Ser Pro Thr Ser Ser Ala Ser Ser Phe Ser Ser Ser Ala Pro Phe Leu
        35                  40                  45

Ala Ser Ala Val Ser Ala Gln Pro Pro Leu Pro Asp Gln Cys Pro Ala
    50                  55                  60

Leu Cys Glu Cys Ser Glu Ala Ala Arg Thr Val Lys Cys Val Asn Arg
65                  70                  75                  80

Asn Leu Thr Glu Val Pro Thr Asp Leu Pro Ala Tyr Val Arg Asn Leu
                85                  90                  95

Phe Leu Thr Gly Asn Gln Leu Ala Val Leu Pro Ala Gly Ala Phe Ala
            100                 105                 110

Arg Arg Pro Pro Leu Ala Glu Leu Ala Ala Leu Asn Leu Ser Gly Ser
        115                 120                 125

Arg Leu Asp Glu Val Arg Ala Gly Ala Phe Glu His Leu Pro Ser Leu
    130                 135                 140

Arg Gln Leu Asp Leu Ser His Asn Pro Leu Ala Asp Leu Ser Pro Phe
145                 150                 155                 160

Ala Phe Ser Gly Ser Asn Ala Ser Val Ser Ala Pro Ser Pro Leu Val
                165                 170                 175

Glu Leu Ile Leu Asn His Ile Val Pro Pro Glu Asp Glu Arg Gln Asn
            180                 185                 190

Arg Ser Phe Glu Gly Met Val Val Ala Ala Leu Leu Ala Gly Arg Ala
        195                 200                 205

Leu Gln Gly Leu Arg Arg Leu Glu Leu Ala Ser Asn His Phe Leu Tyr
    210                 215                 220

Leu Pro Arg Asp Val Leu Ala Gln Leu Pro Ser Leu Arg His Leu Asp
225                 230                 235                 240
```

```
Leu Ser Asn Asn Ser Leu Val Ser Leu Thr Tyr Val Ser Phe Arg Asn
            245                 250                 255

Leu Thr His Leu Glu Ser Leu His Leu Glu Asp Asn Ala Leu Lys Val
            260                 265                 270

Leu His Asn Gly Thr Leu Ala Glu Leu Gln Gly Leu Pro His Ile Arg
            275                 280                 285

Val Phe Leu Asp Asn Asn Pro Trp Val Cys Asp Cys His Met Ala Asp
        290                 295                 300

Met Val Thr Trp Leu Lys Glu Thr Glu Val Val Gln Gly Lys Asp Arg
305                 310                 315                 320

Leu Thr Cys Ala Tyr Pro Glu Lys Met Arg Asn Arg Val Leu Leu Glu
                325                 330                 335

Leu Asn Ser Ala Asp Leu Asp Cys Asp Pro Ile Leu Pro Pro Ser Leu
                340                 345                 350

Gln Thr Ser Tyr Val Phe Leu Gly Ile Val Leu Ala Leu Ile Gly Ala
            355                 360                 365

Ile Phe Leu Leu Val Leu Tyr Leu Asn Arg Lys Gly Ile Lys Lys Trp
        370                 375                 380

Met His Asn Ile Arg Asp Ala Cys Arg Asp His Met Glu Gly Tyr His
385                 390                 395                 400

Tyr Arg Tyr Glu Ile Asn Ala Asp Pro Arg Leu Thr Asn Leu Ser Ser
                405                 410                 415

Asn Ser Asp Val
            420
```